United States Patent
Stewart et al.

(10) Patent No.: US 11,266,647 B2
(45) Date of Patent: Mar. 8, 2022

(54) METHOD FOR INCREASING CELL PROLIFERATION IN PANCREATIC BETA CELLS, TREATMENT METHOD, AND COMPOSITION

(71) Applicant: ICAHN SCHOOL OF MEDICINE AT MOUNT SINAI, New York, NY (US)

(72) Inventors: Andrew F. Stewart, New York, NY (US); Peng Wang, Fresh Meadows, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 0 days.

(21) Appl. No.: 16/344,230

(22) PCT Filed: Oct. 26, 2017

(86) PCT No.: PCT/US2017/058498
§ 371 (c)(1),
(2) Date: Apr. 23, 2019

(87) PCT Pub. No.: WO2018/081401
PCT Pub. Date: May 3, 2018

(65) Prior Publication Data
US 2019/0328738 A1    Oct. 31, 2019

Related U.S. Application Data

(60) Provisional application No. 62/413,071, filed on Oct. 26, 2016.

(51) Int. Cl.
*A61K 31/47* (2006.01)
*A61K 31/44* (2006.01)
(Continued)

(52) U.S. Cl.
CPC ........ *A61K 31/519* (2013.01); *A61K 31/4045* (2013.01); *A61K 31/428* (2013.01);
(Continued)

(58) Field of Classification Search
CPC .......................... A61K 31/437; A61K 31/4709
(Continued)

(56) References Cited

U.S. PATENT DOCUMENTS

2004/0116474 A1* 6/2004 Munchhof .............. A61P 13/12
514/341
2004/0192583 A1* 9/2004 Medicherla .............. A61P 9/12
514/266.1

(Continued)

FOREIGN PATENT DOCUMENTS

WO    2013/119518 A1    8/2013
WO    2014058080 A1    4/2014

(Continued)

OTHER PUBLICATIONS

Dhawan et al. "Inhibition of TGF-beta singaling promotes human pancreatic beta-cell replication," Diabetes, May 2016, vol. 65, pp. 1208-1218. (Year: 2016).*

(Continued)

*Primary Examiner* — Shengjun Wang
(74) *Attorney, Agent, or Firm* — Troutman Pepper Hamilton Sanders LLP (Rochester)

(57) ABSTRACT

The present invention relates to a method of increasing cell proliferation in a population of pancreatic beta cells and a method of treating a subject for a condition associated with an insufficient level of insulin secretion. Also disclosed is a composition. The composition includes a dual-specificity tyrosine phosphorylation-regulated kinase 1A (DYRK1 A)
(Continued)

inhibitor and a transforming growth factor beta (TGFβ) superfamily signaling pathway inhibitor.

24 Claims, 23 Drawing Sheets

Specification includes a Sequence Listing.

(51) Int. Cl.
| | |
|---|---|
| A61K 31/425 | (2006.01) |
| A61K 31/40 | (2006.01) |
| A61K 31/519 | (2006.01) |
| A61P 1/18 | (2006.01) |
| A61P 3/10 | (2006.01) |
| A61K 31/4045 | (2006.01) |
| A61K 31/428 | (2006.01) |
| A61K 31/437 | (2006.01) |
| A61K 31/454 | (2006.01) |
| A61K 31/4709 | (2006.01) |
| C12N 5/071 | (2010.01) |

(52) U.S. Cl.
CPC .......... *A61K 31/437* (2013.01); *A61K 31/454* (2013.01); *A61K 31/4709* (2013.01); *A61P 1/18* (2018.01); *A61P 3/10* (2018.01); *C12N 5/0676* (2013.01); *C12N 2501/999* (2013.01)

(58) Field of Classification Search
USPC .................. 514/314, 292, 367, 422, 333
See application file for complete search history.

(56) References Cited

U.S. PATENT DOCUMENTS

| | | | | |
|---|---|---|---|---|
| 2010/0173931 | A1* | 7/2010 | Ellies | A61K 45/06 514/300 |
| 2011/0053930 | A1* | 3/2011 | Yu | A61P 9/10 514/233.2 |
| 2011/0123651 | A1* | 5/2011 | Mower | A23L 2/68 424/732 |
| 2013/0210060 | A1* | 8/2013 | Hosoya | A61P 3/10 435/29 |
| 2016/0186143 | A1 | 6/2016 | Melton et al. | |

FOREIGN PATENT DOCUMENTS

| | | |
|---|---|---|
| WO | 2015/157093 A1 | 10/2015 |
| WO | 2017/168245 A1 | 10/2017 |

OTHER PUBLICATIONS

Nassar et al. "A TGF-beta receptor 1 inhibitor for prevention of proliferative vitreoretinopathy," Experimental Eye Research, 2014, vol. 123, pp. 72-86. (Year: 2014).*

Xiao et al. "Resveratrol attenuates renal injury and fibrosis by inhibiting transforming growth factor β pathway on matrix metalloproteinase 7," Experimental Biology and Medicine, Jan. 2016, vol. 241, pp. 140-146. (Year: 2016).*

Wang et al., "Diabetes Mellitus—Advances and Challenges in Human β-Cell Proliferation," Nat. Rev. Endocrinol.11:201-212 (2015).

EP Search Report and Opinion for EP Application No. 178636361.1, dated May 6, 2020.

Shen et al., "Inhibition of DYRK1A and GSK3B induces human β-cell proliferation," Nature Comm. 6:8372 (2015).

Madhu et al., "Dual Inhibition of Activin/Nodal/TGF-β and BMP Signaling Pathways by SB431542 and Dorsomorphin Induces Neuronal Differentiation of Human Adipose Derived Stem Cells," Stem Cells International 1-13 (2016).

Vogt et al.,"The Specificities of Small Molecule Inhibitors of the TGFβ and BMP Pathways," Cellular Signaling 23(11):1831-1842 (2011).

Wang et al., "Combined Inhibition of DYRK1A, SMAD, and Trithorax Pathways Synergizes to Induce Robust Replication in Adult Human Beta Cells," Cell Metab. 29(3):638-652 (2018).

Rosado-Olivieri et al., "Identification of a LIF-Responsive, Replication-Competent Subpopulation of Human beta Cells," Cell Metab. 31(2):327-338 (2020).

Office Action in Europe Application No. 17863636.1, dated Jan. 12, 2021.

Wang et al., "A High-throughput Chemical Screen Reveals That Harmine-mediated Inhibition of DYRK1A Increases Human Pancreatic Beta Cell Replication," Nature Medicine 21(4):383-388 (2015).

Huynh et al., "Screening and Identification of a Novel Class of TGF-[beta] Type 1 Receptor Kinase Inhibitor," Journal of Biomolecular Screening 16(7):724-733 (2011).

Dhawan et al., "Inhibition of TGF-beta Signaling Promotes Human Pancreatic Beta Cell Replication," Diabetes 65(5):1208-1218 (2016).

Pagliuca et al., "Generation of Functional Human Pancreatic [beta] Cells In Vitro," Cell 159(2):428-439 (2014).

PCT International Search Report and Opinion for corresponding PCT/US2017/058498, dated Jan. 9, 2018.

Office Action in Europe Application No. 17863636.1, dated Oct. 22, 2021.

* cited by examiner

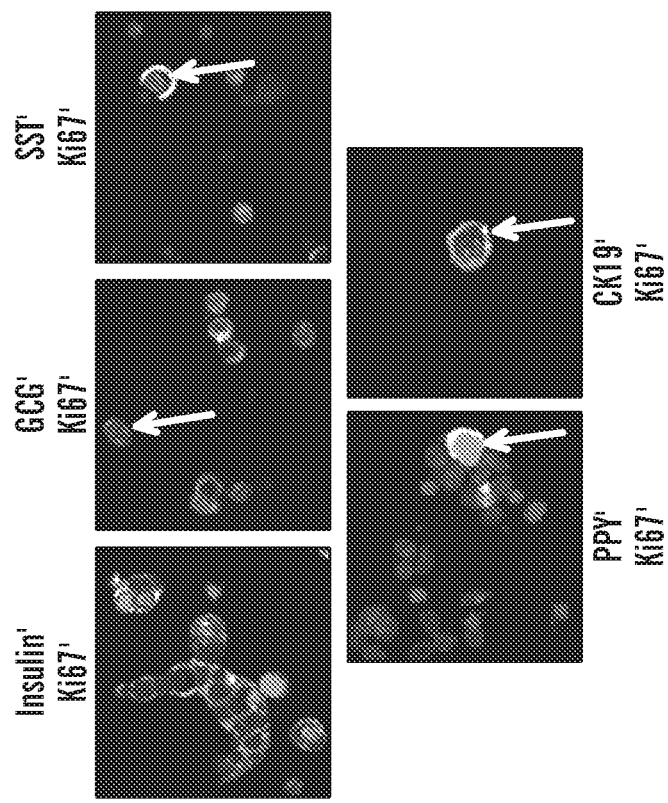
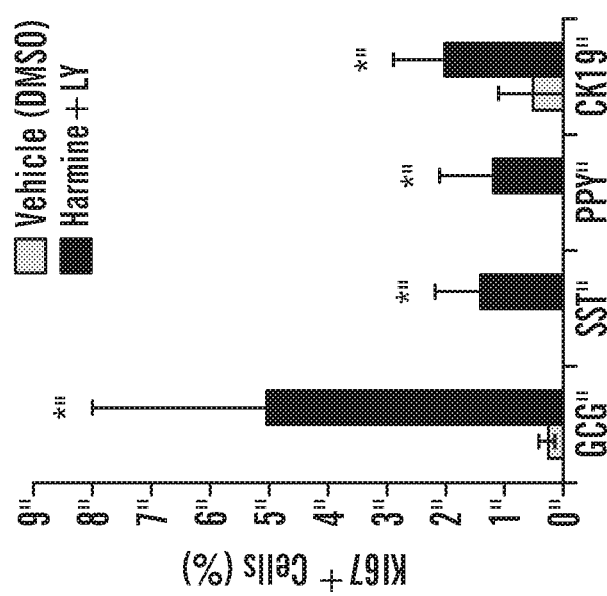
FIG. 3B
FIG. 3A

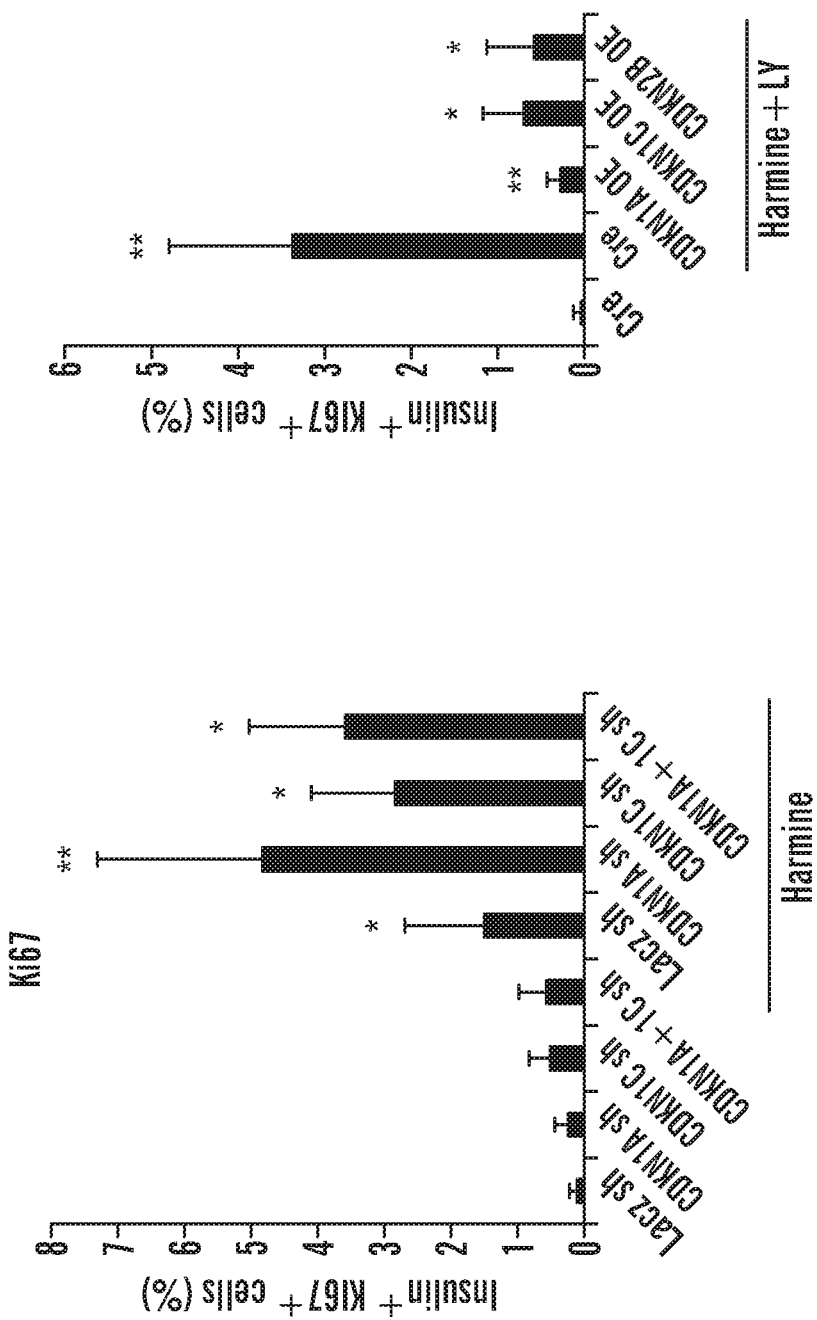

METHOD FOR INCREASING CELL PROLIFERATION IN PANCREATIC BETA CELLS, TREATMENT METHOD, AND COMPOSITION

This application is a national stage application under 35 U.S.C. § 371 of PCT International Application Ser. No. PCT/US2017/058498, filed Oct. 26, 2017, which claims the priority benefit of U.S. Provisional Patent Application Ser. No. 62/413,071, filed Oct. 26, 2016, which are hereby incorporated by reference in their entirety.

This invention was made with government support under grant numbers DK104211 and DK020541 awarded by the National Institutes of Health. The government has certain rights in the invention.

FIELD OF THE INVENTION

Disclosed herein is a method for increasing cell proliferation in a population of pancreatic beta cells, a method of treating a subject for a condition associated with a lowered or deficient level of insulin secretion, and a composition for carrying out such methods.

BACKGROUND OF THE INVENTION

Loss of beta cell mass is a primary cause of diabetes. In type 1 diabetes ("T1D"), a person's beta cell mass is reduced because that patient's immune system attacks and destroys his or her own beta cells, which leaves the person dependent on exogenously administered insulin for survival. For people diagnosed with type 2 diabetes ("T2D"), beta cell mass tends to be relatively low before onset of the disease, and loss of beta cell mass is accelerated after onset of the disease due to glucose toxicity caused by insulin resistance. Thus, the induction of beta cell proliferation would be desirable to restore beta cell mass to normal in people with T1D—and above normal in people with T2D.

The present inventors have previously induced human beta cell proliferation using small molecule inhibitors of the enzyme Dual-Specificity Tyrosine-Regulated Kinase 1A ("DYRK1A"). Harmine, INDY, GNF4877, and 5-iodotubericidin (5-IT) induce human beta cell proliferation in the range of 1.5% to 3% per day. This rate of proliferation matches the highest rate of proliferation in human beta cells that occurs during the first year of life, which is the only stage of human development at which appreciable beta cell proliferation occurs.

Unfortunately, a human beta cell proliferation rate of 1.5% to 3% is clearly insufficient for a practical therapy to treat T1D and T2D patients. The present inventors hypothesize that, to increase beta cell mass within a therapeutically reasonable time period, the beta cell proliferation rate will need to be at least about 5% per day, which is a daily rate that was heretofore unachievable.

SUMMARY OF THE INVENTION

In one aspect, the present invention relates to a method of increasing cell proliferation in a population of pancreatic beta cells. This method involves contacting a population of pancreatic beta cells with a dual-specificity tyrosine phosphorylation-regulated kinase 1A ("DYRK1A") inhibitor and a transforming growth factor beta ("TGFβ") superfamily signaling pathway inhibitor under conditions effective to increase cell proliferation in the population of pancreatic beta cells.

In another aspect, the present invention relates to a method of treating a subject for a condition associated with an insufficient level of insulin secretion. This method involves administering to a subject in need of treatment for a condition associated with an insufficient level of insulin secretion a dual-specificity tyrosine phosphorylation-regulated kinase 1A ("DYRK1A") inhibitor and a TGFβ superfamily signaling pathway inhibitor under conditions effective to increase pancreatic beta cell mass in the subject to treat the subject for an insufficient level of insulin secretion.

A further aspect of the present invention relates to a composition comprising a dual-specificity tyrosine phosphorylation-regulated kinase 1A ("DYRK1A") inhibitor and a transforming growth factor beta ("TGFβ") superfamily signaling pathway inhibitor.

The present invention provides alternative strategies for the treatment of a condition associated with a lowered or deficient level of insulin secretion (e.g., metabolic syndrome, T1D, and T2D) through the use of small molecule drugs to induce residual pancreatic beta cell regeneration, thereby restoring adequate insulin secretion (Wang et al., "Advances and Challenges in Human Beta Cell Proliferation for Diabetes," *Nature Rev. Endocrinology* 11:201-212 (2015); Cozar-Castellano et al., "Induction of Beta Cell Proliferation and Retinoblastoma Protein Phosphorylation in Rat and Human Islets Using Adenoviral Delivery of Cyclin-dependent Kinase-4 and Cyclin $D_1$," *Diabetes* 53:149-59 (2004); Fiaschi-Taesch et al., "Developing A Human Pancreatic Beta Cell G1/S Molecule Atlas," *Diabetes* 62:2450-59 (2013); Fiaschi-Taesch et al., "Cytoplasmic-Nuclear Trafficking of G1/S Cell Cycle Molecules and Adult Human Beta Cell Replication: A Revised Model of Human Beta Cell G1/S Control," *Diabetes* 62:2460-70 (2013); and Wang et al., "A High-Throughput Chemical Screen Reveals That Harmine-Mediated Inhibition of DYRK1A Increases Human Pancreatic Beta Cell Replication," *Nature Medicine* 21:383-388 (2015), which are hereby incorporated by reference in their entirety). The examples of the present application (infra) demonstrate that combined pharmacologic or genetic inhibition of DYRK1A and TGFβSF signaling induces remarkable and previously unattainable "rates" of human beta cell proliferation.

BRIEF DESCRIPTION OF THE DRAWINGS

FIG. 1A shows the effects of harmine alone, and of various TGFβSF ligand inhibitors, some of which are specific for TGFβ receptors, and others for activin, inhibin, and BMP receptors. As reported previously (Wang et al., "A High-Throughput Chemical Screen Reveals That Harmine-Mediated Inhibition of DYRK1A Increases Human Pancreatic Beta Cell Replication," *Nature Medicine* 21:383-388 (2015); Shen et al., "Inhibition of DYRK1A and GSK3B Induces Human Beta Cell Proliferation," *Nature Comm.* 6:8372 (2015); Dirice et al., "Inhibition of DYRK1A Stimulates Human Beta Cell Proliferation," *Diabetes* 65:1660-71 (2016); Aamodt et al., "Development of a Reliable Automated Screening System to Identify Small Molecules and Biologics That Promote Human Beta Cell Regeneration," *AJP Endo. Metab.* 311:E859-68 (2016); and Wang et al., "Singe Cell Mass Cytometry Analysis of Human Endocrine Pancreas," *Cell Metabolism* 24:616-26 (2016), which are hereby incorporated by reference in their entirety), harmine induces Ki67 labeling in approximately 2% of normal human beta cells, and TGFβSF inhibitors lead to only marginal Ki67 labeling. However, all of the TGFβSF inhibitors in combination with harmine induce striking increases in Ki67 labeling in beta cells. The large error bars reflect the diversity in health and other qualities commonly observed in cadaver-derived human islets, but indicate that in some human adult human islet preparations, Ki67 could be observed in as many as 15-20% of insulin-positive cells. Each bar represents experiments in 4-10 sets of human islets, and error bars indicate mean±SEM. *indicates p. 0.05 vs. control, and **indicates p<0.05 vs. harmine treatment alone. FIG. 1B shows examples of human islets, treated with DMSO (above) or the harmine-LY364947 combination (below), immunolabeled for insulin and Ki67, revealing unprecedented rates of proliferation. In some beta cells, Ki67-positive nuclear doublets can be observed indicating cell division is in process.

FIGS. 2A-2B show the effects of two other harmine analogues, INDY (Wang et al., "A High-Throughput Chemical Screen Reveals That Harmine-Mediated Inhibition of DYRK1A Increases Human Pancreatic Beta Cell Replication," *Nature Medicine* 21:383-388 (2015), which is hereby incorporated by reference in its entirety) (FIG. 2A) and leucettine-41 (FIG. 2B) (Tahtough et al., "Selectivity, Cocrystal Structures, and Neuroprotective Properties of Leucettines, a Family of Protein Kinase Inhibitors Derived from the Marine Sponge Alkaloid Leucettamine B," *J. Med. Chem.* 55:9312-30 (2012), which is hereby incorporated by reference in its entirety) on human beta cell labeling with Ki67. FIG. 2C shows a dose-response curve of a fixed maximal dose of harmine (10 μM) (Wang et al., "A High-Throughput Chemical Screen Reveals That Harmine-Mediated Inhibition of DYRK1A Increases Human Pancreatic Beta Cell Replication," *Nature Medicine* 21:383-388 (2015), which is hereby incorporated by reference in its entirety) together with increasing doses of the TGFβ receptor inhibitor, LY364947. The combined effects of harmine plus LY364947 far exceed the effects of a maximal dose of either compound alone, providing evidence for synergistic effects of the combined treatments. FIGS. 2D-2F show the effects of harmine and LY364947 alone or in combination on human islets using BrdU (FIGS. 2D-2E) and phospho-histone-3 ("PHH3") (FIGS. 2F-2G). Note that PHH3 captures only G2M phases of cell cycle, as compared to Ki67 and BrdU, which capture all phases of cell cycle, so that labeling indices for PHH3 are lower than for Ki67 and BrdU. In all experiments, bars represent 3-10 human islet preparations, and error bars represent mean±SEM. *indicates p. 0.05 vs. control, and **indicates p<0.05 vs. harmine treatment alone.

FIGS. 3A-3E show the effects of the harmine-TGFβSF combination on proliferation in non-beta cells in the human islet, and on beta cell survival. FIG. 3A shows the quantification of Ki67 immmunolabeling in alpha cells (GCG), delta cells (STS), PP cells (PP), and ductal (CK19) cells in four different sets of human islets treated with DMSO (vehicle) or 10 μM harmine and 5 μM LY364947. Error bars indicate SEM. *indicates p<0.05 as determined by Student's T-test. FIG. 3B is a fluorescence microscopy image showing examples of Ki67 labeling in non-beta islet cells in human islets. Cells are immunolabeled with Ki67, Glucagon ("GCG"), somatostatin ("STS"), pancreatic polypeptide ("PP"), and/or the ductal cell marker CK19, as indicated. FIGS. 3C-3D are a fluorescence microscopy image (FIG. 3C) and bar graph showing (FIG. 3D) of human islets which were dispersed, plated, and treated for 96 hours with vehicle (0.1% DMSO) harmine (10 μM) plus LY364947 (5 μM), and then examined for cell death using TUNEL labeling. There are occasional TUNEL-positive beta and non-beta cells in the control islets, but these are rare in the islets treated with the harmine-LY364947 combination. FIG. 3E shows the quantification of TUNEL labeling in 2,000 beta cells from four different donors. Beta cell death was not increased in the drug-treated beta cells, and even appears to be lower than in controls, although this did not achieve statistical significance. Error bars represent mean±SEM.

FIGS. 4A-4B illustrate the effects of harmine and the harmine-LY364947 combination treatment for four days on key beta cell transcription factors (FIG. 4A) and markers of beta cell differentiation (FIG. 4B) in whole human islets. Representative of five human islet preparations; error bars indicate mean±SEM. **indicates p<0.05 vs. vehicle (DMSO) treatment. FIG. 4C shows immunocytochemistry on dispersed human beta cells showing that combination treatment increases PDX1, NKX6.1, and MAFA specifically in beta cells, and is representative of experiments in three different human islet donor preparations. FIG. 4D shows insulin secretion in response to low and high glucose in islets from eight different donors in the presence of vehicle, harmine, LY364947, or the harmine-LY364947 combination. Error bars indicate mean±SEM. *indicates p<0.05 for high glucose vs. low glucose. FIGS. 4E-4F show the effects of harmine, LY364947, GW788388, or ALK5 inhibitor on beta cell Ki67 immunolabeling (FIG. 4E) and key beta cell transcription factors and differentiation markers in islets from four donors with T2D (FIG. 4F). Error bars indicate mean±SEM. *indicates p<0.05.

FIG. 5A shows immunoblots of control, harmine-, LY364947, ALK5 inhibitor- or combination-treated whole human islets. While SMAD2 and SMAD3 (detected by the same antibody) did not change, p-SMAD3 was reduced by harmine, and further reduced by LY364947 or ALK5 inhibitor and the combinations. SMAD1, 5, and 9 are also detected by a common antibody, and are reduced by harmine and the drug combinations. The immunoblots are representative of separate experiments in human islets from three different donors. FIG. 5B shows the effects of a control adenovirus expressing LacZ and adenoviruses silencing SMAD2, 3, and 4 (150 moi each) on Ki67 immunolabeling in harmine-treated human islets. FIG. 5C shows the effects of adenoviral SMAD6 and SMAD7 overexpression (100 moi) on beta cell proliferation alone and in combination with harmine. FIG. 5D is an example of the mitogenic effects of SMAD7 silencing in human beta cells on Ki67 immunolabeling. FIG. 5E shows the effect of adenoviral DYRK1A overexpression or a control adenovirus expressing Cre (Ad.Cre) on proliferation in human islets treated with the harmine-LY364947 combination. FIG. 5F shows examples of Ad.Cre and Ad.DYRK1A overexpressing viruses on Ki67 immunolabeling in human islets treated with harmine and LY364947. FIG. 5G shows the effects of adenoviral silencing of DYRK1A in combination with TGFβSF inhibitors GW788388 or LY364947. Ad.shLacZ indicates a sh-adenovirus for the Ad.shDYRK1A. Bars are representative of 4-5 human islet preparations, and error bars represent mean±SEM. *indicates p. 0.05 vs. control, and **indicates p<0.05 vs. adenoviral SMAD7 treatment alone.

FIGS. 6A-6G illustrate cell cycle molecule changes in response to harmine, LY364947, ALK5 inhibitor, and the combination of harmine and LY364947. FIG. 6A shows the effects on vehicle (DMSO 0.1%), harmine (10 μM), LY364947 (5 μM), or the combination of harmine and LY364947 on gene expression in whole human islets for cell cycle activators, as assessed using qPCR. FIG. 6B shows comparable results for cell cycle inhibitors. FIG. 6C shows immunoblots for p15INK2b, p16INK2a, p57KIP, and p21CIP in human islet treated with harmine, LY364947, or the combination of harmine and LY364947. FIGS. 6D-6E show the effect of silencing SMADs 2,3,4 or overexpressing SMADs 6 and/or 7 on expression of CDKN1A (FIG. 6D) and CDKN1C (FIG. 6E) in human islets as assessed using qPCR. FIG. 6F shows the effects of silencing CDKN1A and CDKN1C on Ki67 immunolabeling in human beta cells in the presence or absence of harmine 10 μM. FIG. 6G shows the effects of overexpression of CDKN1A, CDKN1C, and CDKN2B on proliferation induced by the combination of harmine and LY364947. All experiments represent five human islet preparations, and error bars represent mean±SEM. *indicates p. 0.05 vs. control, and **indicates p<0.05 vs. control.

FIGS. 7A-7B are schematics of the human CDKN1A (FIG. 7A) and CDKN1C (FIG. 7B) loci from hg19 UCSC genome browser, showing primer pairs used for ChIP in the small black boxes, the gene bodies in blue below, and enhancers and promotors in orange and black respectively. FIGS. 7C-7D show that ChIP results in control (white bars) and harmine-LY364947-treated (black bars) human islets, with primer pairs corresponding to CDKN1A (FIG. 7C) and CDKN1C (FIG. 7D) along the x-axis. Error bars indicate SEM. Each experiment represents the mean of a minimum of three sets of human islets. FIGS. 7E-7F are schematics indicating interactions of the SMADs and Trithorax members under basal conditions (FIG. 7E) and following harmine-LY364947 treatment (FIG. 7F), illustrating that the combination of harmine and LY364947 treatment markedly alters and in most cases disrupts SMAD-Trithorax binding to the CDKN1A and CDKN1C loci.

FIG. 8A shows that in the canonical TGFβ paradigm, ligands such as TGFβ, activins, inhibins, myostatin, GDF11, and bone morphogenic proteins ("BMPs") bind to multi-subunit receptors which phosphorylate and thereby activate so called receptor SMADs (SMADs 2 and 3, and 1,5,8/9). These are then able to heteromerize with SMAD4, a common SMAD, and the SMAD4 heteromers translocate to the nucleus where, among other things, they are incorporated into the chromatin-modifying and DNA-methylating Trithorax Complex and, thereby, influence expression of multiple gene families. Adapted from Brown and Schneyer, "Emerging Roles for the TGFb Superfamily in Pancreatic Beta Cell Homeostasis," *Trends Endocrinol. Metab.* 21:441-448 (2010), which is hereby incorporated by reference in its entirety. FIG. 8B shows a simplified illustration of the synergistic mechanisms through which harmine and TGFβSF pathway inhibitors cooperate to enhance human beta cell proliferation. Harmine acting on DYRK1A primarily activates cyclins, CDKs, and related cell cycle activators. In parallel, TFβSF pathway inhibitors relieve activation of cell cycle inhibitors including CDKN1A encoding p21CIP, CDKN1C encoding p57KIP, and CDKN2B encoding p15INK4.

In FIG. 9A, three month old male C57BL6N mice were administered vehicle (DMSO), harmine, GW788388, or the combination of harmine plus GW788388 intraperitoneally in the doses shown for seven days, after which mice were sacrificed, the pancreata harvested, fixed, and immunolabeled from insulin abd Ki67 as described in Wang et al., "A High-Throughput Chemical Screen Reveals that Harmine-Mediated Inhibition of DYRK1A Increases Human Pancreatic Beta Cell Replication," *Nature Med.* 21:383-388 (2015), which is hereby incorporated by reference in its entirety. FIG. 9B shows an experiment in which 500 adult human cadaveric islets from one human donor were transplanted into the renal capsule of NOD-SCID mice, and allowed to engraft for one week. On day seven, treatment was begun exactly as in FIG. 9A for seven days.

DETAILED DESCRIPTION OF THE INVENTION

Figure 1A:
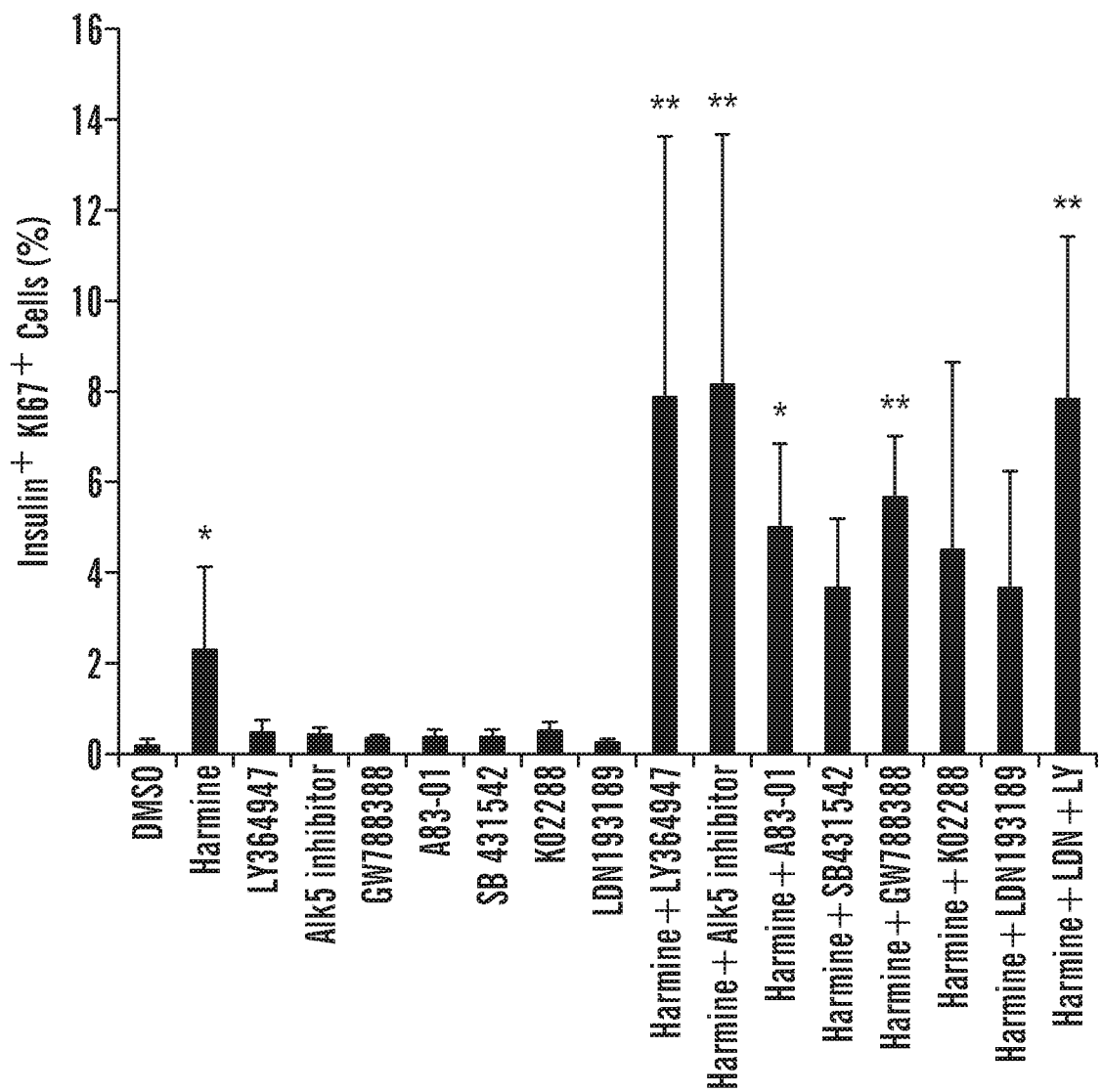
FIGS. 1A-1B show the induction of human beta cell proliferation by combined harmine and TGFβSF inhibitor treatment.

The present invention relates to a method for increasing cell proliferation in a population of pancreatic beta cells, a method of treating a subject for a condition associated with a lowered or deficient level of insulin secretion, and a composition for carrying out such methods.

One aspect of the present invention relates to a method of increasing cell proliferation in a population of pancreatic beta cells. This method involves contacting a population of pancreatic beta cells with a dual-specificity tyrosine phosphorylation-regulated kinase 1A ("DYRK1A") inhibitor and a transforming growth factor beta ("TGFβ") superfamily signaling pathway inhibitor under conditions effective to increase cell proliferation in the population of pancreatic beta cells.

This method may be carried out ex vivo or in vivo. When carried out ex vivo, a population of pancreatic beta cells may be, according to one embodiment, provided by obtaining beta cells from a pancreas and culturing the cells in a liquid medium suitable for the in vitro or ex vivo culture of mammalian cells, in particular human cells. For example and without limitation a suitable and non-limiting culture medium may be based on a commercially available medium such as RPMI1640 from Invitrogen.

If needed, methods for determining whether a cell has a pancreatic beta cell phenotype are known in the art and include, without limitation, incubating the cell with glucose and testing whether insulin expression in the cell is increased or induced. Other methods include testing whether beta cell specific transcription factors are expressed, the detection of beta cell specific gene products with the help of RNA quantitative PCR, the transplantation of a candidate cell in diabetic mice, and subsequent testing of the physiologic response following said transplantation as well analyzing the cells with electron microscopy.

According to one embodiment, the method is carried out ex vivo and cultured pancreatic beta cells are contacted with a dual-specificity tyrosine phosphorylation-regulated kinase 1A ("DYRK1A") inhibitor and a transforming growth factor beta ("TGFβ") superfamily signaling pathway inhibitor under conditions effective to increase cell proliferation in the population of cultured pancreatic beta cells.

According to another embodiment, the method is carried out in vivo and a population of pancreatic beta cells in a subject, e.g., a human subject, are contacted with a dual-specificity tyrosine phosphorylation-regulated kinase 1A ("DYRK1A") inhibitor and a transforming growth factor beta ("TGFβ") superfamily signaling pathway inhibitor by administering to the subject the dual-specificity tyrosine phosphorylation-regulated kinase 1A ("DYRK1A") inhibitor and a transforming growth factor beta ("TGFβ") superfamily signaling pathway inhibitor under conditions effective to increase cell proliferation in pancreatic beta cells in the subject.

Contacting a population of pancreatic beta cells with a DYRK1A inhibitor and TGFβ superfamily signaling pathway inhibitor may be carried out sequentially or simultaneously using a composition comprising one or both of the DYRK1A inhibitor and/or TGFβ superfamily signaling pathway inhibitor.

DYRK1A inhibitors are known in the art and include, without limitation, those listed in Table 1, below.

The DYRK1A inhibitors used in carrying out this and other methods of the present invention may be a small molecule inhibitor of DYRK1A. In a specific embodiment, the DYRK1A inhibitor used in carrying out this and other methods of the present invention is selected from harmine, INDY, leucettine, 5-iodotubercidin ("5-IT"), and GNF4877.

TGFβ superfamily signaling pathway inhibitors include small molecules and other (e.g., neutralizing monoclonal antibodies, synthetic/recombinant peptide inhibitors, and siRNA) inhibitors of the BMP family of receptors, activin and inhibin receptors, and related receptors.

TGFβ superfamily signaling pathway inhibitors are also known in the art and include, without limitation, SB431542, SB505124, A-83-01, Decorin, soluble TGF-β receptor, Ier-

TABLE 1

DYRK1A Inhibitors

| Source | DYRK1A Inhibitors |
|---|---|
| U.S. Pat. No. 9,446,044* | Epigallocatechin-gallate (EGCG), harmine, thiazolo[5,4-f]quinazoline compounds |
| U.S. Pat. No. 9,447,093* | Harmine, leucettamine B, chromenones, 3,5-harmine, epigallocatechin-3-gallate (EGCG), diaryl-7-azaindoles |
| Tahtouh et al., "Selectivity, Cocrystal Structures, and Neuroprotective Properties of Leucettines, a Family of Protein Kinase InhibitorsDerived from the Marine Sponge Alkaloid Leucettamine B," *J. Med. Chem.* 55(21): 9312-30 (2012)* | Leucettines |
| Koo et al., "QSAR analysis of pyrazolidine-3,5-diones derivatives," *Bioorg. Med. Chem. Lett.* 19: 2324-8 (2009)* | pyrazolidine-3,5-diones derivatives |
| PCT Publication No. WO/2012/098068* | pyrazolo[3,4-d]pyrimidines |
| U.S. patent application Pub. No. 12/884,480* | indoloquinoline compounds |
| De la Torre et al., "Epigallocatechin-3-gallate, a DYRK1A inhibitor, rescues cognitive deficits in Down syndrome mouse models and in humans," *Mol. Nutr. Food Res.* (2013)* | Epigallocatechin-3-gallate |
| Ionescu et al., "DYRK1A Kinase Inhibitors with Emphasis on Cancer," *Mini-Reviews in Med. Chem.* (2012)* | Pyrazolidine-3,5-dione derivatives; Pyrrole-2,5-dione derivatives; Imidazolone (Leucettamine) derivatives; Thia-3,4-diazole derivatives; Pyridine derivatives; Purine derivatives and analogs (e.g., Purvalanol A, Roscovitine, N-&-N 1, N-&-N 2); Benzothiazole derivatives (e.g., INDY, TG003); 4,5,6,7-Tetrabromobenzimidazole (TBI) derivatives and analogs (e.g., TBB, TBI, DMAT); 3-Carboxy-4(1H)-quinolone derivatives; 4-amino-6-arylquinazolin derivatives; Quinoline derivatives; Meriolins (3-(4-pyrimidinyl)-7-azaindole); Aminopyrimidinylindole Derivatives; 1H-Imidazo[4,5-c]pyridin-2-yl)-3-amino-1,2,5-oxadiazole derivatives; Pyrazolo[1,5-a]-1,3,5-triazine derivatives; beta-Carbolines; Quinazolinone; *Piper methysticum* (Kava) derivatives; Flavokavain A, EGCG, Apigenin, Emodin, Quinalizarin |
| Becker et al., "Activation, Regulation, and Inhibition of DYRK1A," *FEBS Journal* (2011)* | Purvanol, Harmine, EGCG, TBB, DMAT, TG003, Pyrazolidine-3,5-dione 21, Pyrazolidine-3,5-dione 18 |
| Kii et al., "Selective Inhibition of the Kinase DYRK1A by Targeting its Folding Process," *Nat. Commm.* 7: 11391 (2016)* | Folding intermediate-selective inhibitor of dual-specificity tyrosine-phosphorylation-regulated kinase 1A (FINDY) |
| Coutadeur et al., "A Novel DYRK1A Inhibitor for the Treatment of Alzheimer's Disease: Effect on Tau and Amyloid Pathologies," *J. Neurochem.* 133: 440-51 (2015)* | EHT 5372 |

*Incorporated herein by reference in its entirety.

delimumab, metelimumab, AP-12009, Follistatin, FLRG, GAST-1, GDF8 propeptide, MYO-029, Noggin, chordin, Cer/Dan, ectodin, and Sclerostin (see Tsuchida et al., "Inhibitors of the TGF-beta Superfamily and their Clinical Applications," *Mini Rev. Med. Chem.* 6(11):1255-61 (2006), which is hereby incorporated by reference in its entirety.

Other inhibitors of TGF-β signaling include, without limitation, 2-(3-(6-Methylpyridin-2-yl)-1H-pyrazol-4-yl)-1,5 napththyridine; [3-(Pyridin-2-yl)-4-(4-quinoyl)]-1H-pyrazole; 3-(6-Methylpyridin-2-yl)-4-(4-quinolyl)-1-phenylthiocarbamoyl-1H-pyrazole; SB-431542; SM16, SB-505124; and 2-(3-(6-Methylpyridin-2-yl)-1H-pyrazol-4-yl)-1,5 napththyridine (ALK5 Inhibitor II) (see U.S. Pat. No. 8,298,825, which is hereby incorporated by reference in its entirety).

An additional type of inhibitor of TGF-β signaling includes, for example, inhibitors of GDF8 and GDF11 (see, e.g., PCT Publication No. WO 2000/043781 and U.S. Pat. No. 6,368,597, which are hereby incorporated by reference in their entirety).

Inhibitors of TGF-β signaling are described in Callahan et al., *J. Med. Chem.* 45:999-1001 (2002); Sawyer et al., *J. Med. Chem.* 46:3953-3956 (2003); Gellibert et al., *J. Med. Chem.* 47:4494-4506 (2004); Tojo et al., *Cancer Sci.* 96:791-800 (2005); Valdimarsdottir et al., *APMIS* 113:773-389 (2005); Petersen et al., *Kidney International* 73:705-715 (2008); Yingling et al., *Nature Rev. Drug Disc.* 3:1011-1022 (2004); Byfield et al., *Mol. Pharmacol.* 65:744-752 (2004); Dumont et al., *Cancer Cell* 3:531-536 (2003); PCT Publication No. WO 2002/094833; PCT Publication No. WO 2004/026865; PCT Publication No. WO 2004/067530; PCT Publication No. WO 2009/032667; PCT Publication No. WO 2004/013135; PCT Publication No. WO 2003/097639; PCT Publication No. WO 2007/048857; PCT Publication No. WO 2007/018818; PCT Publication No. WO 2006/018967; PCT Publication No. WO 2005/039570; PCT Publication No. WO 2000/031135; PCT Publication No. WO 1999/058128; U.S. Pat. Nos. 6,509,318; 6,090,383; 6,419,928; 9,927,738; 7,223,766; 6,476,031; 6,419,928; 7,030,125; 6,943,191, U.S. Patent Application Publication No. 2005/0245520; U.S. Patent Application Publication No. 2004/0147574; U.S. Patent Application Publication No. 2007/0066632; U.S. Patent Application Publication No. 2003/0028905; U.S. Patent Application Publication No. 2005/0032835; U.S. Patent Application Publication No. 2008/0108656; U.S. Patent Application Publication No. 2004/015781; U.S. Patent Application Publication No. 2004/0204431; U.S. Patent Application Publication No. 2006/0003929; U.S. Patent Application Publication No. 2007/0155722; U.S. Patent Application Publication No. 2004/0138188, and U.S. Patent Application Publication No. 2009/0036382, which are hereby incorporated by reference in their entirety.

Exemplary inhibitors of TGF-β signaling include, but are not limited to, AP-12009 (TGF-β Receptor type II antisense oligonucleotide); Lerdelimumab (CAT 152, antibody against TGF-β Receptor type II); GC-1008 (antibody to all isoforms of human TGF-β); ID11 (antibody to all isoforms of murine TGF-β); soluble TGF-β; soluble TGF-β Receptor type II; dihydropyrroloimidazole analogs (e.g., SKF-104365); triarylimidazole analogs (e.g., SB-202620 (4-(4-(4-fluorophenyl)-5-(pyridin-4-yl)-1H-imidazol-2-yl)benzoic acid) and SB-203580 (4-(4-Fluorophenyl)-2-(4-methyl sulfinyl phenyl)-5-(4-pyridyl)-1H-imidazole)); RL-0061425; 1,5-naphthyridine aminothiazole and pyrazole derivatives (e.g., 4-(6-methyl-pyridin-2-yl)-5-(1,5-naphthyridin-2-yl)-1,3-thiazole-2-amine and 2-[3-(6-methyl-pyridin-2-yl)-1H-pyrazole-4-yl]-1,5-naphthyridine); SB-431542 (4-(5-Benzol[1,3]dioxol-5-yl-4-pyridin-2-yl-1H-imidazol-2-yl)-benzamide); GW788388 (4-(4-(3-(pyridin-2-yl)-1H-pyrazol-4-yl)pyridin-2-yl)-N-(tetrahydro-2H-pyran-4-yl) benzamide); A-83-01 (3-(6-Methyl-2-pyridinyl)-N-phenyl-4-(4-quinolinyl)-1H-pyrazole-1-carbothioamide); Decorin; Lefty 1; Lefty 2; Follistatin; Noggin; Chordin; Cerberus; Gremlin; Inhibin; BIO (6-bromo-indirubin-3'-oxime); Smad proteins (e.g., Smad6, Smad7); and Cystatin C.

Inhibitors of TGF-β signaling also include molecules which inhibit TGF-β Receptor type I. Inhibitors of TGF-β Receptor type I include, but are not limited to, soluble TGF-β Receptor type I; AP-11014 (TGF-β Receptor type I antisense oligonucleotide); Metelimumab (CAT 152, TGF-β Receptor type I antibody); LY550410; LY580276 (3-(4-fluorophenyl)-5,6-dihydro-2-(6-methylpyridin-2-yl)-4H-pyrrolo[1,2-b]pyrazole); LY364947 (4-[3-(2-Pyridinyl)-1H-pyrazol-4-yl]-quinoline); LY2109761; LY573636 (N-((5-bromo-2-thienyl)sulfonyl)-2,4-dichlorobenzamide); SB-505124 (2-(5-Benzo[1,3]dioxol-5-yl-2-tert-butyl-3H-imidazol-4-yl)-6-methylpyridine); SD-208 (2-(5-Chloro-2-fluorophenyl)-4-[(4-pyridyl)amino]pteridine); SD-093; KI2689; SM16; FKBP12 protein; and 3-(4-(2-(6-methylpyridin-2-yl)H-imidazo[1,2-a]pyridin-3-yl)quinolin-7-yloxy)-N,N-dimethylpropan-1-amine.

Inhibitors of TGF-β Receptor type I are described in Byfield and Roberts, *Trends Cell Biol.* 14:107-111 (2004); Sawyer et al., *Bioorg. Med. Chem. Lett.* 14:3581-3584 (2004); Sawyer et al., *J. Med. Chem.* 46:3953-3956 (2003); Byfield et al., *Mol. Pharmacol.* 65:744-752 (2004); Gellibert et al., *J. Med. Chem.* 47:4494-4506 (2004); Yingling et al., *Nature Rev. Drug Disc.* 3:1011-1022 (2004); Dumont et al., *Cancer Cell* 3:531-536 (2003); Tojo et al., *Cancer Sci.* 96:791-800 (2005); PCT Publication No. WO 2004/026871; PCT Publication No. WO 2004/021989; PCT Publication No. WO 2004/026307; PCT Publication No. WO 2000/012497, U.S. Pat. Nos. 5,731,424; 5,731,144; 7,151,169; U.S. Patent Application Publication No. 2004/00038856 and U.S. Patent Application Publication No. 2005/0245508, all of which are herein incorporated in their entirety.

In one embodiment, the TGFβ superfamily signaling pathway inhibitor used in carrying out this and other methods of the present invention includes compounds that interfere with TGFβ superfamily ligands, receptors, and/or downstream signaling molecules (e.g., SMADs), or nuclear targets (e.g., chromatin modifying complexes and transcription factors). See FIGS. 1A-1B.

In one embodiment, the TGFβ superfamily signaling pathway inhibitor may be antisera that neutralize, e.g., TGFβ ligand.

In another embodiment, the TGFβ superfamily signaling pathway inhibitor is selected from the group consisting of an inhibitor of TGFβ/TGFβ receptor binding, activin or inhibin/activin receptor binding, and bone morphogenetic protein ("BMP")/BMP receptor binding.

In a specific embodiment, the TGFβ superfamily signaling pathway inhibitor is an inhibitor of TGFβ/TGFβ receptor binding selected from the group consisting of LY364947 and GW788388.

In another specific embodiment, the TGFβ superfamily signaling pathway inhibitor used in carrying out this and other methods of the present invention is an inhibitor of activin or inhibin/activin receptor binding selected from the group consisting of SB431542 and Alk5 inhibitor II. Additional exemplary inhibitors of activin or inhibin/activin receptor binding may be selected from the group consisting of SB-505124, BYM388, follistatin, follistatin-related protein (FSRP), follistatin domains (i.e., Fs2, Fs12, Fs123), A-83-01, Cripto, GW788388, BAMBI, and Sotatercept (see Byfield et al., "SB-505124 is a Selective Inhibitor of Transforming Growth Factor-Beta Type I Receptors ALK4, ALK5, and ALK7," Mol. Pharmacol. 65(3):744-52 (2004); Lach-Trifilieffa et al., "An Antibody Blocking Activin Type II Receptors Induces Strong Skeletal Muscle Hypertrophy and Protects from Atrophy," Mol. Cell. Biol. 34(4):606-18 (2014); Zhang et al., "Inhibition of Activin Signaling Induces Pancreatic Epithelial Cell Expansion and Diminishes Terminal Differentiation of Pancreatic β-Cells," Diabetes 53(8):2024-33 (2004); Harrington et al., "Structural Basis for the Inhibition of Activin Signalling by Follistatin," EMBO J. 25(5):1035-45 (2006); Tojo et al., "The ALK-5 Inhibitor A-83-01 Inhibits Smad Signaling and Epithelial-to-Mesenchymal Transition by Transforming Growth Factor-Beta," Cancer Sci. 96(11):790-800 (2005); Yan et al., "Human BAMBI Cooperates with Smad7 to Inhibit Transforming Growth Factor-Beta Signaling," J. Biol. Chem. 284(44):30097-104 (2009); Tan et al., "Targeted Inhibition of Activin Receptor-Like Kinase 5 Signaling Attenuates Cardiac Dysfunction Following Myocardial Infarction," Am. J. Physiol. Heart Circ. Physiol. 298(5):H1415-25 (2010); and Gokoffski et al., "Activin and GDF11 Collaborate in Feedback Control of Neuroepithelial Stem Cell Proliferation and Fate," Develop. 138(19):4131-42 (2011), which are hereby incorporated by reference in their entirety).

In another specific embodiment, the TGFβ superfamily signaling pathway inhibitor used in carrying out this and other methods of the present invention is an inhibitor of BMP/BMP receptor binding. An exemplary inhibitor of BMP/BMP receptor binding is LDN193189. Additional exemplary BMP inhibitors may be selected from the group consisting of noggin, sclerostin, chordin, CTGF, follistatin, gremlin, inhibin, DMH1, DMH2, Dorsomorphin, K02288, LDN212854, DM 3189, BMP-3, and BAMBI (see PCT Publication No. WO 2014/018691 A1 and Mohedas et al., "Development of an ALK2-Biased BMP Type I Receptor Kinase Inhibitor," ACS Chem. Biol. 8(6):1291-302 (2013); Yan et al., "Human BAMBI Cooperates with Smad7 to Inhibit Transforming Growth Factor-Beta Signaling," J. Biol. Chem. 284(44):30097-104 (2009), which are hereby incorporated by reference in their entirety).

According to another embodiment, the TGFβ superfamily signaling pathway inhibitor is a SMAD signaling pathway inhibitor. Exemplary SMAD signaling pathway inhibitors may be selected from the group including, without limitation, SMAD3 siRNA, SMAD 2/3 siRNA, PD169316, SB203580, SB202474, specific inhibitor of Smad3 (SIS3), HSc025, and SB525334 (see Qureshi et al., "Smad Signaling Pathway is a Pivotal Component of Tissue Inhibitor of Metalloproteinases-3 Regulation by Transforming Growth Factor Beta in Human Chondrocytes," BBA Mol. Cell Res. 1783(9):1605-12 (2008); Hasegawa et al., "A Novel Inhibitor of Smad-Dependent Transcriptional Activation Suppresses Tissue Fibrosis in Mouse Models of Systemic Sclerosis," Arthritis Rheum. 60(11):3465-75 (2009); and Ramdas et al., "Canonical Transforming Growth Factor-β Signaling Regulates Disintegrin Metalloprotease Expression in Experimental Renal Fibrosis via miR-29," Am. J. Pathol. 183(6):1885-96 (2013), which are hereby incorporated by reference in their entirety).

Additional exemplary SMAD signaling pathway inhibitors include, without limitation, miR-100, LDN 193189, SMAD-binding peptide aptamers (e.g., Trx-FoxH1, Trx-Le1, Trx-CBP, Trx-SARA), pirfenidone, and LDN193189 (see Fu et al., "MicroRNA-100 Inhibits Bone Morphogenetic Protein-Induced Osteoblast Differentiation by Targeting Smad," Eur. Rev. Med. Pharmacol. Sci. 20(18):3911-19 (2016); Boergermann et al., "Dorsomorphin and LDN-193189 Inhibit BMP-Mediated Smad, p38 and Akt signalling in C2C12 Cells," Int. J. Biochem. Cell Biol. 42(11): 1802-7 (2010); Cui et al., "Selective Inhibition of TGF-Responsive Genes by Smad-Interacting Peptide Aptamers from FoxH1, Lef1 and CBP," Oncogene 24:3864-74 (2005); Zhao et al., "Inhibition of Transforming Growth Factor-Beta1-Induced Signaling and Epithelial-to-Mesenchymal Transition by the Smad-Binding Peptide Aptamer Trx-SARA," Mol. Biol. Cell 17:3819-31 (2006); Li et al., "Oral Pirfenidone Protects Against Fibrosis by Inhibiting Fibroblast Proliferation and TGF-β Signaling in a Murine Colitis Model," Biochem. Pharmacol. 117:57-67 (2016); and Cook et al., "BMP Signaling Balances Murine Myeloid Potential Through SMAD-Independent p38MAPK and NOTCH Pathways," Blood 124(3):393-402 (2014), which are hereby incorporated by reference in their entirety).

In another specific embodiment, the TGFβ superfamily signaling pathway inhibitor is an inhibitor of the trithorax complex. Exemplary trithorax complex inhibitors include, without limitation, WDR5-0103, MI-1, MI-2, MI-2-2, MLS001171971-01, ML227, MCP-1, RBB5 siRNA, and MLL1 siRNA (see Senisterra et al., "Small-Molecule Inhibition of MLL Activity by Disruption of its Interaction with WDR5," Biochem. J. 449(1):151-9 (2013); Cierpicki et al., "Challenges and Opportunities in Targeting the Menin-MLL Interaction," Future Med. Chem. 6(4):447-62 (2014); Lee et al., "Roles of DPY30 in the Proliferation and Motility of Gastric Cancer Cells," PLOS One 10(7):e0131863 (2015); and Zhou et al., "Combined Modulation of Polycomb and Trithorax Genes Rejuvenates β Cell Replication," J. Clin. Invest. 123(11):4849-4858 (2013), which are hereby incorporated by reference in their entirety).

In another embodiment, the TGFβ superfamily signaling pathway inhibitor is an inhibitor or activator of the polycomb repressive complex 2 ("PRC2"). Exemplary PRC2 inhibitors include GSK926, EPZ005687, GSK126, GSK343, E11, UNC1999, EPZ6438, Constellation Compound 3, EZH2 siRNA, and 3-deazaneplanocin A (see Verma et al., "Identification of Potent, Selective, Cell-Active Inhibitors of the Histone Lysine Methyltransferase EZH2," ACS Med. Chem. Lett. 3:1091-6 (2012); Xu et al., "Targeting EZH2 and PRC2 Dependence as Novel Anticancer Therapy," Exp. Hematol. 43:698-712 (2015); Knutson et al., "A Selective Inhibitor of EZH2 Blocks H3K27 Methylation and Kills Mutant Lymphoma Cells," Nat. Chem. Biol. 8:890-6 (2012); Qi et al., "Selective Inhibition of Ezh2 by a Small Molecule Inhibitor Blocks Tumor Cells Proliferation," Proc. Natl Acad. Sci. USA 109:21360-65 (2012); McCabe et al., "EZH2 Inhibition as a Therapeutic Strategy for Lymphoma with EZH2-Activating Mutations," Nature 492:108-12 (2012); Nasveschuk et al., "Discovery and Optimization of Tetramethylpiperidinyl Benzamides as Inhibitors of EZH2," ACS Med. Chem. Lett. 5:378-83 (2014); Brooun et al., "Polycomb Repressive Complex 2 Structure with Inhibitor Reveals a Mechanism of Activation and Drug Resistance," Nature Comm. 7:11384 (2016); Fiskus et al., "Histone Deacetylase Inhibitors Deplete Enhancer of Zeste 2 and Associated Polycomb Repressive Complex 2 Proteins in Human Acute Leukemia Cells," Mol. Cancer Ther. 5(12): 3096-104 (2006); and Fiskus et al., "Combined Epigenetic Therapy with the Histone Methyltransferase EZH2 Inhibitor 3-Deazaneplanocin A and the Histone Deacetylase Inhibitor Panobinostat Against Human AML Cells," Blood 114(13): 2733-43 (2009), which are hereby incorporated by reference in their entirety.) In one embodiment, activation of PRC2 is achieved by genetic overexpression of PRC members, e.g., EZH2 (Chen et al., "Polycomb Protein Ezh2 Regulates Pancreatic Beta-Cell Ink4a/ARf Expression and Regeneration in Diabetes Mellitus, "*Genes Dev.* 23(8):975-985 (2009) and Wang et al., "Insights Into Beta Cell Regeneration for Diabetes Via Integration of Molecular Landscapes in Human Insulinomas," *Nature Communications,* 8:767 (2017), which are hereby incorporated by reference in their entirety), BMI1 (Dhawan et al., "Bmi-1 Regulates the Ink4a/Arf Locus to Control Pancreatic β-Cell Proliferation," *Genes Dev.* 23(8): 906-911 (2009), which is hereby incorporated by reference in its entirety), and YY1 (Wang et al., "Insights Into Beta Cell Regeneration for Diabetes Via Integration of Molecular Landscapes in Human Insulinomas," *Nature Communications,* 8:767 (2017), which is hereby incorporated by reference in its entirety).

In another embodiment, contacting is carried out with the DYRK1A inhibitor harmine and the TGFβ superfamily signaling pathway inhibitor LY364947. Alternatively, contacting is carried out with the DYRK1A inhibitor harmine and the TGFβ superfamily signaling pathway inhibitor LDN193189.

According to one embodiment, "pancreatic beta cells" are primary human pancreatic beta cells. The primary human pancreatic beta cells may be cadaveric cells. In one embodiment, the "pancreatic beta cells" are stem-cell derived (see, e.g., U.S. Patent Application Publication No. 2016/0175363 and U.S. Pat. No. 9,394,523, which are hereby incorporated by reference in their entirety).

In one embodiment of carrying out this and other methods of the present invention, contacting does not induce beta cell death or DNA damage.

Moreover, contacting may induce beta cell differentiation and increase glucose-stimulated insulin secretion. Beta cell de-differentiation is known to contribute to the inability of beta-cells to sense glucose or secrete insulin (Talchai et al., "Pancreatic β Cell Dedifferentiation as a Mechanism of Diabetic β Cell Failure," *Cell* 150:1223-34 (2012) and Cinti et al., "Evidence of Beta Cell Dedifferentiation in Human Type 2 Diabetes," *J. Clin. Endocrinol. Metab.* 101:1044-54 (2016), which are hereby incorporated by reference in their entirety). Thus, in one embodiment, contacting induces beta cell differentiation.

In another embodiment, the method is carried out to enhance cell survival. For example, the method may be carried out to enhance cell survival of a treated population of cells relative to an untreated population of cells. Alternatively, the method may be carried out to decrease cell death or apoptosis of a treated population of cells relative to an untreated population of cells.

In another aspect, the present invention relates to a method of treating a subject for a condition associated with an insufficient level of insulin secretion. This method involves administering to a subject in need of treatment for a condition associated with an insufficient level of insulin secretion a dual-specificity tyrosine phosphorylation-regulated kinase 1A ("DYRK1A") inhibitor and a TGFβ superfamily signaling pathway inhibitor under conditions effective to increase pancreatic beta cell mass in the subject to treat the subject for an insufficient level of insulin secretion.

As used herein, a condition associated with an insufficient level of insulin secretion means a condition where a subject produces a lower plasma level of insulin than is required to maintain normal glucose levels in the blood such that the subject with the condition associated with insufficient insulin secretion becomes hyperglycemic. In such a condition, the pancreatic beta cells of the afflicted subject secrete an insufficient level of insulin to maintain the presence of a normal or adequate concentration of glucose in the blood (i.e., normoglycemica).

According to one embodiment, one of the conditions associated with an insufficient level of insulin secretion is insulin resistance. Insulin resistance is a condition in which a subject's cells become less sensitive to the glucose-lowering effects of insulin. Insulin resistance in muscle and fat cells reduces glucose uptake (and, therefore, local storage of glucose as glycogen and triglycerides), whereas insulin resistance in liver cells results in reduced glycogen synthesis and storage and a failure to suppress glucose production and release into the blood. Insulin resistance normally refers to reduced glucose-lowering effects of insulin. However, other functions of insulin can also be affected. For example, insulin resistance in fat cells reduces the normal effects of insulin on lipids and results in reduced uptake of circulating lipids and increased hydrolysis of stored triglycerides. Increased mobilization of stored lipids in these cells elevates free fatty acids in the blood plasma. Elevated blood fatty-acid concentrations, reduced muscle glucose uptake, and increased liver glucose production all contribute to elevated blood glucose levels. If insulin resistance exists, more insulin needs to be secreted by the pancreas. If this compensatory increase does not occur, blood glucose concentrations increase and T2D occurs.

According to another embodiment, one of the conditions associated with an insufficient level of insulin secretion is diabetes. Diabetes can be divided into two broad types of diseases: type I ("T1D" or "type 1") and type II ("T2D" or "type 2"). The term "diabetes" also refers herein to a group of metabolic diseases in which patients have high blood glucose levels, including T1D, T2D, gestational diabetes, congenital diabetes, cystic fibrosis-related diabetes, steroid diabetes, and several forms of monogenic diabetes.

According to another embodiment, a condition associated with an insufficient level of insulin secretion is metabolic syndrome. Metabolic syndrome is generally used to define a constellation of abnormalities that is associated with increased risk for the development of type II diabetes and atherosclerotic vascular disease. Related conditions and symptoms include, but are not limited to, fasting hyperglycemia (diabetes mellitus type II or impaired fasting glucose, impaired glucose tolerance, or insulin resistance), high blood pressure; central obesity (also known as visceral, male-pattern, or apple-shaped adiposity), meaning overweight with fat deposits mainly around the waist; decreased HDL cholesterol; and elevated triglycerides.

Other conditions that may be associated with an insufficient level of insulin secretion include, without limitation, hyperuricemia, fatty liver (especially in concurrent obesity) progressing to non-alcoholic fatty liver disease, polycystic ovarian syndrome (in women), and acanthosis nigricans.

Related disorders may also be treated pursuant to this aspect of the invention and such disorders include, without limitation, any disease associated with a blood or plasma glucose level outside the normal range, preferably hyperglycemia. Consequently, the term "related disorders" includes impaired glucose tolerance ("IGT"), impaired fasting glucose ("IFG"), insulin resistance, metabolic syndrome, postprandial hyperglycemia, and overweight/obesity. Such related disorders can also be characterized by an abnormal blood and/or plasma insulin level.

According to another embodiment, this method of the present invention is carried out to treat a subject with conditions associated with beta cell failure. Such conditions include, without limitation, pancreatitis, cystic fibrosis, pancreatectomy, and glucocorticoid treatment.

In carrying out this method of the present invention, a dual-specificity tyrosine phosphorylation-regulated kinase 1A ("DYRK1A") inhibitor and a TGFβ superfamily signaling pathway inhibitor are administered under conditions effective to increase pancreatic beta cell mass in the subject to treat the subject for a condition associated with an insufficient level of insulin secretion.

According to one embodiment, a DYRK1A inhibitor and TGFβ superfamily signaling pathway inhibitor are administered to increase pancreatic beta cell mass in the subject, which will result in an increased level of insulin secretion in the subject.

The DYRK1A inhibitor and TGFβ superfamily signaling pathway inhibitor are, according to one embodiment, formulated as separate pharmaceutical compositions or a single pharmaceutical composition comprising both the DYRK1A inhibitor and TGFβ superfamily signaling pathway inhibitor. According to one embodiment, such pharmaceutical composition(s) comprises a therapeutically effective amount of the DYRK1A inhibitor and/or TGFβ superfamily signaling pathway inhibitor.

Thus, according to one embodiment, this method of the present invention may be carried out by administering a combination or combinatorial therapy or treatment of a DYRK1A inhibitor and TGFβ superfamily signaling pathway inhibitor. The terms "combination" or "combinatorial therapy" or "combinatory treatment" mean a treatment where at least two compounds are co-administered to a subject to cause a biological effect, in this case a synergistic effect. In a combinatorial therapy, the at least two drugs may be administered together or separately, at the same time or sequentially. Simultaneous administration is not required, as long as the drugs produce a synergistic effect in the subject as described infra in the examples to improve the subject's conditions. Also, the at least two drugs may be administered through different routes and protocols. As a result, although they may be formulated together, the drugs of a combination may also be formulated separately.

In carrying out this method of the present invention, administering of compounds to a subject may involve administering pharmaceutical compositions containing the compound(s) (i.e., a DYRK1A inhibitor and TGFβ superfamily signaling pathway inhibitor) in therapeutically effective amounts, which means an amount of compound effective in treating the stated conditions and/or disorders in the subject. Such amounts generally vary according to a number of factors well within the purview of ordinarily skilled artisans. These include, without limitation, the particular subject, as well as its age, weight, height, general physical condition, and medical history; the particular compound used, as well as the carrier in which it is formulated and the route of administration selected for it; the length or duration of treatment; and the nature and severity of the condition being treated.

Administering typically involves administering pharmaceutically acceptable dosage forms, which means dosage forms of compounds described herein (i.e., a DYRK1A inhibitor and TGFβ superfamily signaling pathway inhibitor) and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., 17$^{th}$ edition, which is hereby incorporated by reference in its entirety.

In carrying out this method of the present invention, the drug (i.e., a DYRK1A inhibitor and TGFβ superfamily signaling pathway inhibitor) may be contained in any appropriate amount in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., *Remington: The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York, which are hereby incorporated by reference in their entirety).

Pharmaceutical compositions according to the present invention may be formulated to release the active drug substantially immediately upon administration or at any predetermined time or time period after administration.

Controlled release formulations include (i) formulations that create a substantially constant concentration of the drug(s) within the body over an extended period of time; (ii) formulations that after a predetermined lag time create a substantially constant concentration of the drug(s) within the body over an extended period of time; (iii) formulations that sustain drug(s) action during a predetermined time period by maintaining a relatively constant, effective drug level in the body with concomitant minimization of undesirable side effects associated with fluctuations in the plasma level of the active drug substance; (iv) formulations that localize drug(s) action by, e.g., spatial placement of a controlled release composition adjacent to or in the diseased tissue or organ; and (v) formulations that target drug(s) action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index ("TI") is defined as the ratio of median lethal dose ($LD_{50}$) to median effective dose ($ED_{50}$)); (ii) a narrow absorption window in the gastro-intestinal tract; or (iii) a very short biological half-life so that frequent dosing during a day is required in order to sustain the plasma level at a therapeutic level.

Any of a number of strategies can be pursued to obtain controlled release in which the rate of release outweighs the rate of metabolism of the drug in question. Controlled release may be obtained by appropriate selection of various formulation parameters and ingredients including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Thus, administering according to this aspect of the invention may be carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Compounds may be administered alone or with suitable pharmaceutical carriers, and can be in solid or liquid form, such as tablets, capsules, powders, solutions, suspensions, or emulsions.

As used herein, the term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

The subject may be a mammalian subject. In one embodiment, the subject is a human subject. Suitable human subjects include, without limitation, children, adults, and elderly subjects having an insulin deficiency.

In other embodiments, the subject may be bovine, ovine, porcine, feline, equine, murine, canine, lapine, etc.

In one embodiment, the administering step may increase the number of proliferating pancreatic beta cells in the subject by at least about 5%, 6%, 7%, 8%, 9%, 10%, or more.

In another embodiment, the administering step my increase the number of proliferating beta cells in the subject by at least about 1% per day, 2% per day, 3% per day, or more.

In some embodiments, the administering increases glucose-stimulated insulin secretion in pancreatic beta cells of the subject.

In one embodiment of this and other aspects of the present invention, the designation of a compound (i.e., a DYRK1A inhibitor and TGFβ superfamily signaling pathway inhibitor as described supra) is meant to designate the compound per se, as well as any pharmaceutically acceptable salt, hydrate, isomer, racemate, ester, or ether thereof. The designation of a compound is meant to designate the compound as specifically designated per se, as well as any pharmaceutically acceptable salt thereof.

Within the context of the present invention, by "treating" it is meant preventive or curative treatment. The term treatment designates in particular the correction, decrease in the rate of change, or reduction of an impaired glucose homeostasis. The level of glucose in blood fluctuates throughout the day. Glucose levels are usually lower in the morning, before the first meal of the day and rise after meals for some hours. Consequently, the term treatment includes the control of blood glucose level by increasing or decreasing blood glucose level depending on the condition of the subject and the daytime in order to reach normal glucose levels. The term treatment more particularly includes a temporary or persistent reduction of blood glucose level in a subject having diabetes or a related disorder. The term "treatment" or "treating" also designates an improvement in insulin release (e.g., by pancreatic beta cells).

As used herein, the phrase "control of blood glucose level" refers to the normalization or the regulation of the blood or plasma glucose level in a subject having abnormal levels (i.e., levels that are below or above a known reference, median, or average value for a corresponding subject with a normal glucose homeostasis).

Another aspect of the present invention relates to a composition comprising a dual-specificity tyrosine phosphorylation-regulated kinase 1A ("DYRK1A") inhibitor and a transforming growth factor beta ("TGFβ") superfamily signaling pathway inhibitor.

DYRK1A inhibitors and a transforming growth factor beta ("TGFβ") superfamily signaling pathway inhibitors are described supra.

In one embodiment, the composition comprises a carrier. The carrier may be a pharmaceutically acceptable carrier as described supra.

EXAMPLES

Materials and Method for Examples 1-6
Chemicals:
Drug sources were as follows: INDY (4997, Tocris Biosciences), BrdU substrate (RPN20, GE Healthcare), Harmine (286044, Sigma), Leucettine-41 (Adipogen, AG-MR-00023-M005), LY364947 (Selleckchem, S2805), Alk5 inhibitor II (Cayman Chemical Co, 446859-33-2), GW788388 (Selleckchem, S2750), A83-01 (Tocris, 2939), SB431542 (Selleckchem, S1067), K02288 (Selleckchem, S7359), LDN193189 (Selleckchem 2618).

Human Pancreatic Islets:
Islets from normal and Type 2 diabetes adult cadaveric pancreas donors were obtained from the NIH/NIDDK-supported Integrated Islet Distribution Program and from the Alberta Diabetes Institute. Depending on the experiments performed, islets were used either as intact islets, or were first dispersed with Accutase (Sigma, St. Louis, Mo.) onto coverslips.

FACS Sorting Human Beta Cells (for Table 2):
Human islets were dispersed and beta cells were labeled with an adenovirus as described previously (Wang et al., "Insights Into Beta Cell Regeneration for Diabetes Via Integration of Molecular Landscapes in Human Insulinomas," *Nature Communications,* 8:767 (2017), which is hereby incorporated by reference in its entirety). Briefly, dispersed human islet cells were transduced 72 hours before harvesting for fluorescence-activated cytometric sorting (FACSAria II) with an adenovirus driven by a RIP1-miniCMV construct that included 177 bases of the hCMV IE-1 promoter ClaI-SpeI fragment ligated to 438 bases of the RIP1 promoter, both upstream of the bright green fluorescent protein ZsGreen (Clontech, Mountain View, Calif.). The beta cell fraction was confirmed to be >92% pure by immunolabeling of sorted cells with insulin, by qRT-PCR and by RNAseq.

Adenoviruses and Transduction:
Adenoviruses were prepared as described previously (Fiaschi-Taesch et al., "Developing A Human Pancreatic Beta Cell G1/S Molecule Atlas," *Diabetes* 62:2450-59 (2013); Fiaschi-Taesch et al., "Cytoplasmic-Nuclear Trafficking of G1/S Cell Cycle Molecules and Adult Human Beta Cell Replication: A Revised Model of Human Beta Cell G1/S Control," *Diabetes* 62:2460-70 (2013); Wang et al., "Insights Into Beta Cell Regeneration for Diabetes Via Integration of Molecular Landscapes in Human Insulinomas," *Nature Communications,* 8:767 (2017); and Cozar-Castellano et al., "Induction of Beta Cell Proliferation and Retinoblastoma Protein Phosphorylation in Rat and Human Islets Using Adenoviral Delivery of Cyclin-Dependent Kinase-4 and Cyclin $D_1$," *Diabetes* 53:149-59 (2004), which are hereby incorporated by reference in their entirety). Unless otherwise described, all transductions were performed using 150 moi for one hour, and studies performed 72 hours later. The sequence and validation of the Ad.DYRK1A and Ad.shDYRK1A have been reported previously (Wang et al., "A High-Throughput Chemical Screen Reveals That Harmine-Mediated Inhibition of DYRK1A Increases Human Pancreatic Beta Cell Replication," *Nature Medicine* 21:383-388 (2015), which is hereby incorporated by reference in its entirety). Adenoviruses encoding human SMAD6 or SMAD7 were prepared as described using cDNAs encoding SMAD6 and SMAD7 obtained from Harvard PlasmID Database. Adenoviruses employed for silencing SMADs 2, 3, and 4 employed the sequences shown in Table 2.

TABLE 2

Adenovirus Sequences

| Name | Sequence | SEQ ID NO: |
|---|---|---|
| Ad.ShSMAD2 | GCTGTAATCTGAAGATCTTCA | SEQ ID NO: 1 |
| Ad.ShSMAD3 | GCAACCTGAAGATCTTCAACA | SEQ ID NO: 2 |
| Ad.sh SMAD4 | GGAATTGATCTCTCAGGATTA | SEQ ID NO: 3 |
| Ad.shp21 | CGCTCTACATCTTCTGCCTTA | SEQ ID NO: 4 |
| Adshp57 | ATTCTGCACGAGAAGGTACAC | SEQ ID NO: 5 | qPCR:

RNA was isolated and quantitative RT-PCR was performed as described previously (Wang et al., "A High-Throughput Chemical Screen Reveals That Harmine-Mediated Inhibition of DYRK1A Increases Human Pancreatic Beta Cell Replication," *Nature Medicine* 21:383-388 (2015), which is hereby incorporated by reference in its entirety). Gene expression in dispersed islets was analyzed by real-time PCR performed on an ABI 7500 System. Primers were as reported previously (Wang et al., "A High-Throughput Chemical Screen Reveals That Harmine-Mediated Inhibition of DYRK1A Increases Human Pancreatic Beta Cell Replication," *Nature Medicine* 21:383-388 (2015), which is hereby incorporated by reference in its entirety).

RNA Sequencing:

RNA from FACS-purified beta cells (Table 3) was prepared immediately using the RNeasy Micro kit (Qiagen).

TABLE 3

RNAseq Profiling of TGFβ Superfamily Members and Receptor in FACS-Sorted Human Beta Cells (RNAseq, FPKM)

| | 1 | 2 | 3 | 4 | 5 |
|---|---|---|---|---|---|
| SMAD1 | 47 | 17 | 59 | 182 | 10 |
| SMAD2 | 14 | 11 | 8 | 20 | 12 |
| SMAD3 | 7 | 1 | 1 | 11 | 1 |
| SMAD4 | 5 | 5 | 4 | 13 | 3 |
| SMAD5 | 8 | 11 | 10 | 55 | 11 |
| SMAD6 | 9 | 5 | 11 | 49 | 3 |
| SMAD7 | 54 | 18 | 132 | 293 | 39 |
| SMAD8/9 | 140 | 20 | 23 | 133 | 22 |
| TGFB1 | 10 | 24 | 81 | 142 | 29 |
| TGFB2 | 4 | 0 | 0 | 1 | 0 |
| TGFB3 | 0 | 1 | 1 | 2 | 0 |
| TGFBI | 170 | 87 | 75 | 88 | 90 |
| TGFBR1 | 5 | 3 | 14 | 82 | 11 |
| TGFBR2 | 4 | 0 | 0 | 11 | 1 |
| TGFBR3 | 10 | 3 | 3 | 67 | 17 |
| BMP2 | 7 | 6 | 8 | 28 | 2 |
| BMP4 | 1 | 0 | 1 | 6 | 1 |
| BMP5 | 39 | 45 | 6 | 60 | 8 |
| BMP6 | 0 | 0 | 0 | 2 | 0 |

TABLE 3-continued

RNAseq Profiling of TGFβ Superfamily Members and Receptor in FACS-Sorted Human Beta Cells (RNAseq, FPKM)

| | 1 | 2 | 3 | 4 | 5 |
|---|---|---|---|---|---|
| BMP7 | 0 | 0 | 0 | 0 | 0 |
| BMPR1B | 0 | 0 | 0 | 1 | 0 |
| BMPR1A | 55 | 13 | 17 | 134 | 15 |
| BMPR2 | 5 | 4 | 15 | 122 | 23 |
| ACVRL1 | 0 | 0 | 0 | 1 | 0 |
| ACVR1B | 97 | 70 | 14 | 28 | 10 |
| ACVR1C | 34 | 16 | 10 | 50 | 21 |
| ACVR1 | 130 | 78 | 53 | 77 | 40 |
| ACVR2A | 16 | 14 | 6 | 18 | 6 |
| ACVR2B | 1 | 0 | 1 | 3 | 1 |
| MSTN | 0 | 0 | 0 | 0 | 0 |
| INHBA | 16 | 19 | 10 | 39 | 15 |
| INHBB | 0 | 0 | 3 | 2 | 1 |
| GDF11 | 6 | 5 | 5 | 10 | 2 |

RNA yields were 300-500 ng from FACS each run, and RNA integrity numbers were between 9.5 and 10.0. PolyA$^+$ mRNA from sorted beta cells was purified with oligo dT magnetic beads. The polyA$^+$ RNA from beta cells was then fragmented in the presence of divalent cations at 94° C. The fragmented RNA was converted into double stranded cDNA. After polishing the ends of the cDNA, the 3' ends were adenylated. Finally, Illumina-supplied universal adapters were ligated to the cDNA fragments. The adaptor ligated DNA was size selected to get an average of 250 bp insert size using AmpPure beads, and amplified by 15 cycle PCR. The PCR DNA was then purified using AmpPure beads to get the final seq library ready for sequencing. The insert size and DNA concentration of the seq library was determined on Agilent Bioanalyzer and Qubit, respectively. A pool of 10 barcoded RNA seq libraries was layered on two of the eight lanes of the Illumina flow cell at appropriate concentration and bridge amplified to yield approximately 25-35 million raw clusters. The DNA reads on the flow cell were then sequenced on HiSEq 2000 using a 100 bp paired end recipe. A similar protocol was used for whole human islets treated with harmine, 10 μg/ml, plus LY364947 diluted in 0.1% DMSO, or vehicle (DMSO 0.1%) alone (Table 4), except that since RNA was more abundant in whole islets, Ribozero-enriched RNA was used.

TABLE 4

Effect of Harmine Treatment of Human Islets on Selected TGFβ Superfamily Members (RNAseq, FPKM)

| | Donor 1 DMSO | Donor 2 DMSO | Donor 1 Harmine | Donor 2 Harmine |
|---|---|---|---|---|
| TGFB1 | 33 | 26 | 24 | 19 |
| TGFBR1 | 13 | 11 | 9 | 8 |
| TGFBR2 | 6 | 4 | 3 | 3 |
| TGFB2 | 8 | 4 | 3 | 2 |
| TGFB1 | 199 | 51 | 62 | 22 |
| INHA | 1 | 2 | 1 | 1 |
| BMP5 | 59 | 42 | 26 | 20 |
| BMP1 | 10 | 5 | 4 | 3 |
| GDF11 | 6 | 6 | 3 | 3 |

Immunocytochemistry and Antisera:

Immunocytochemistry was performed on 4% paraformaldehyde fixed (15 minutes), Accutase-dispersed human islets plated on coverslips as described (Wang et al., "A High-Throughput Chemical Screen Reveals That Harmine-Mediated Inhibition of DYRK1A Increases Human Pancreatic Beta Cell Replication," *Nature Medicine* 21:383-388

(2015); Fiaschi-Taesch et al., "Developing A Human Pancreatic Beta Cell G1/S Molecule Atlas," *Diabetes* 62:2450-59 (2013); Fiaschi-Taesch et al., "Cytoplasmic-Nuclear Trafficking of G1/S Cell Cycle Molecules and Adult Human Beta Cell Replication: A Revised Model of Human Beta Cell G1/S Control," *Diabetes* 62:2460-70 (2013); Wang et al., "Insights Into Beta Cell Regeneration for Diabetes Via Integration of Molecular Landscapes in Human Insulinomas," *Nature Communications,* 8:767 (2017); and Cozar-Castellano et al., "Induction of Beta Cell Proliferation and Retinoblastoma Protein Phosphorylation in Rat and Human Islets Using Adenoviral Delivery of Cyclin-Dependent Kinase-4 and Cyclin $D_1$," *Diabetes* 53:149-59 (2004), which are hereby incorporated by reference in their entirety). Primary antisera were: BrdU (ab6326, Abcam), Ki67 (RM-9106-sl, Thermo Scientific, and MIB1, DAKO), p-Histone-3 (06-570, Millipore), insulin (A0564, DAKO), p-yH2AX (MA1-2022, Thermo Scientific), NKX6.1 (F55A10-c, University of Iowa), PDX1 (07-696, Millipore), MAFA (Ab26405, Abcam), Glucagon (2760s, Cell Signaling), Somatostatin (Sc-20999, Santa Cruz), Pancreatic Polypeptide (A0619, DAKO), and CK19 (Ab52625, Abcam). Species-specific mouse Alexa Fluor 488 (A-11029, Life Technologies), rat Alexa Fluor 594 (A-11007, Life Technologies), rabbit Alexa Fluor 488 (A11037, Life Technologies) or guinea pig Alexa Fluor 488 (A-11073, Life Technologies) secondary antisera were selected as appropriate. TUNEL labeling was performed as described (Wang et al., "A High-Throughput Chemical Screen Reveals That Harmine-Mediated Inhibition of DYRK1A Increases Human Pancreatic Beta Cell Replication," *Nature Medicine* 21:383-388 (2015); Fiaschi-Taesch et al., "Developing A Human Pancreatic Beta Cell G1/S Molecule Atlas," *Diabetes* 62:2450-59 (2013); Fiaschi-Taesch et al., "Cytoplasmic-Nuclear Trafficking of G1/S Cell Cycle Molecules and Adult Human Beta Cell Replication: A Revised Model of Human Beta Cell G1/S Control," *Diabetes* 62:2460-70 (2013); Wang et al., "Insights Into Beta Cell Regeneration for Diabetes Via Integration of Molecular Landscapes in Human Insulinomas," *Nature Communications,* 8:767 (2017); and Cozar-Castellano et al., "Induction of Beta Cell Proliferation and Retinoblastoma Protein Phosphorylation in Rat and Human Islets Using Adenoviral Delivery of Cyclin-Dependent Kinase-4 and Cyclin $D_1$," *Diabetes* 53:149-59 (2004), which are hereby incorporated by reference in their entirety).

Immunoblots: Immunoblots were performed on whole human islets as described in detail previously (Meier et al., "Beta Cell Replication is the Primary Mechanism Subserving the Postnatal Expansion of Beta Cell Mass in Humans," *Diabetes* 57:1584-94 (2008); Kassem et al., "Beta-Cell Proliferation and Apoptosis in the Developing Normal Human Pancreas and in Hyperinsulinism of Infancy," *Diabetes* 49:1325-1333 (2000); Wang et al., "Advances and Challenges in Human Beta Cell Proliferation for Diabetes," *Nature Rev. Endocrinology* 11:201-212 (2015); and Fiaschi-Taesch et al., "Developing A Human Pancreatic Beta Cell G1/S Molecule Atlas," *Diabetes* 62:2450-59 (2013), which are hereby incorporated by reference in their entirety). Primary antisera employed were: SMAD2/3 (Cell Signaling, 8685p), p-SMAD3 (Abcam, ab52903), SMAD4 (Sc-7966, Santa Cruz), SMAD1/5/9 (ab66737, Abcam), p15INK4 (Abcam, ab53034), p16INK4a (Sc-468, Santa Cruz), p21CIP (556430, BD), p57CIP2 (2557s, Cell Signaling) and GAPDH (Sc-25778, Santa Cruz).

Glucose-Stimulated Insulin Secretion:

GSIS was performed as described previously (Wang et al., "A High-Throughput Chemical Screen Reveals That Harmine-Mediated Inhibition of DYRK1A Increases Human Pancreatic Beta Cell Replication," *Nature Medicine* 21:383-388 (2015); Fiaschi-Taesch et al., "Developing A Human Pancreatic Beta Cell G1/S Molecule Atlas," *Diabetes* 62:2450-59 (2013); Fiaschi-Taesch et al., "Cytoplasmic-Nuclear Trafficking of G1/S Cell Cycle Molecules and Adult Human Beta Cell Replication: A Revised Model of Human Beta Cell G1/S Control," *Diabetes* 62:2460-70 (2013); Wang et al., "Insights Into Beta Cell Regeneration for Diabetes Via Integration of Molecular Landscapes in Human Insulinomas," *Nature Communications,* 8:767 (2017); and Cozar-Castellano et al., "Induction of Beta Cell Proliferation and Retinoblastoma Protein Phosphorylation in Rat and Human Islets Using Adenoviral Delivery of Cyclin-Dependent Kinase-4 and Cyclin $D_1$," *Diabetes* 53:149-59 (2004), which are hereby incorporated by reference in their entirety). Briefly, whole human islets were cultured in low glucose (2.8 mM) or high glucose (16.8 mM) for 30 minutes, and media harvested and assayed for insulin (Mercodia). Results are expressed as fold change in media insulin concentration in high glucose as compared to the low glucose concentration.

Chromatin Immunoprecipitation Assay:

ChIP was performed using the EZ-ChIP Kit (Millipore) according to the manufacturer's protocol as described previously (Wang et al., "Insights Into Beta Cell Regeneration for Diabetes Via Integration of Molecular Landscapes in Human Insulinomas," *Nature Communications,* 8:767 (2017), which is here by incorporated by reference in its entirety). Human cadaveric islets were dispersed as described previously. A minimum of three separate islet preparations were used for each figure shown. $2\times10^6$ cells were collected per experiment for each SMAD2/3, SMAD4, KDM6A, and MEN1 immunoprecipitation. Immunoprecipitated DNA was quantified using ABI 7500 real-time quantitative PCR detection system (Life Technologies). The following antibodies were used: anti-SMAD2/3 (Cell Signaling #8685), anti-SMAD4 (R&D Systems #AF2097), anti-KDM6A (Abcam #ab84190), and anti-MEN1 (Bethyl Laboratories Inc. #A300-105A). Data are presented as ChIP reads normalized relative to input controls, and fold-enrichment divided by respective IgG. Error bars indicate mean±SEM. The primer sets for CDKN1C were described previously (Wang et al., "Insights Into Beta Cell Regeneration for Diabetes Via Integration of Molecular Landscapes in Human Insulinomas," *Nature Communications,* 8:767 (2017), which is here by incorporated by reference in its entirety). The primer sets for CDKN1A were as shown in Table 5.

TABLE 5

| CDKN1A Primers | | |
|---|---|---|
| Name | Primer Sequence | SEQ ID NO: |
| CDKN1A_1 Forward Primer | ATGATCTCAGCTCACTGCAA | SEQ ID NO: 6 |
| CDKN1A_1 Reverse Primer | ACAGGGTCAGGAGTTTTGAG | SEQ ID NO: 7 |

TABLE 5-continued

CDKN1A Primers

| Name | Primer Sequence | SEQ ID NO: |
|---|---|---|
| CDKN1A_2 Forward Primer | GGCTGCCTCTGCTCAATAATG | SEQ ID NO: 8 |
| CDKN1A_2 Reverse Primer | CCAGCACTTCCTCTCCCTT | SEQ ID NO: 9 |
| CDKN1A_3 Forward Primer | CTCCCCAAAGTAAACAGAC | SEQ ID NO: 10 |
| CDKN1A_3 Reverse Primer | CCAGCCCTTTGGATGGTTTG | SEQ ID NO: 11 |
| CDKN1A_4 Forward Primer | CTGCTGGAACTCGGCCAGGCTCAG | SEQ ID NO: 12 |
| CDKN1A_4 Reverse Primer | TGAGCTGCGCCAGCTGAGGTGTGA | SEQ ID NO: 13 |
| CDKN1A_5 Forward Primer | CTAAAACAAGGGTTTGCG | SEQ ID NO: 14 |
| CDKN1A_5 Reverse Primer | CTAGATCCTAGTCCTGTCTTGAAC | SEQ ID NO: 15 |
| CDKN1A_6 Forward Primer | ACTTGTCCCTAGGAAAATCC | SEQ ID NO: 16 |
| CDKN1A_6 Reverse Primer | GAAAACGGAGAGTGAGTTTG | SEQ ID NO: 17 |

Mouse Pancreas Studies:

Male C57BL/6N mice (12 week-old) received vehicle (saline), 10 mg kg$^{-1}$ harmine HCl, 30 mg kg$^{-1}$ GW788388 or the combination of harmine and GW788388 by intraperitoneal injection daily for 7 days. Mice were sacrificed on day 7, pancreata harvested, fixed in 10% neutral buffered formalin, paraffin embedded, and sectioned. Sections were stained for Ki-67 and insulin as previously reported (Wang et al., "A High-Throughput Chemical Screen Reveals that Harmine-Mediated Inhibition of DYRK1A Increases Human Pancreatic Beta Cell Replication," Nature Medicine 21:383-388 (2015), which is hereby incorporated by reference in its entirety). A minimum of 2,000 beta cells per pancreas were counted. Investigators were blinded as to group assignments.

Human Islet Transplant Studies:

500 human islet equivalents from adult human pancreas organ donors were transplanted under the renal capsule of NOD-SCID mice as described in detail in (Wang et al., "A High-Throughput Chemical Screen Reveals that Harmine-Mediated Inhibition of DYRK1A Increases Human Pancreatic Beta Cell Replication," Nature Medicine 21:383-388 (2015), which is hereby incorporated by reference in its entirety). Mice were allowed to recover for 7 days and then treated with vehicle (saline), 10 mg kg-1 harmine HCl, 30 mg kg-1 GW788388 or the combination of harmine and GW788388 by intraperitoneal injection daily for 7 days. Mice were sacrificed on day 7, renal grafts harvested, fixed in 10% neutral buffered formalin, paraffin embedded and sectioned. Sections were stained for Ki-67 and insulin as previously reported (Wang et al., "A High-Throughput Chemical Screen Reveals that Harmine-Mediated Inhibition of DYRK1A Increases Human Pancreatic Beta Cell Replication," Nature Medicine 21:383-388 (2015), which is hereby incorporated by reference in its entirety).

Statistics:

Statistics were performed using Student's unpaired, two-tailed T-test or by One-Way Analysis of Variance as described in the Brief Description of the Drawings. P values less than 0.05 were considered to be significant.

Figure 1B:
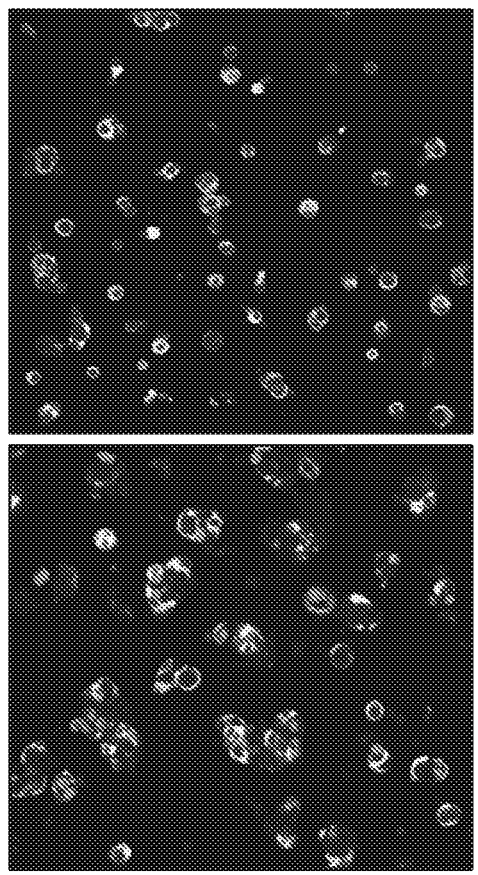

Example 1—Combinations of DYRK1A Inhibitors and TGFβSF Inhibitors Induce Unprecedented and Synergistic Human Beta Cell Proliferation Gene expression profiles from FACS-sorted human beta cells (Wang et al., "Wang et al., "Insights Into Beta Cell Regeneration for Diabetes Via Integration of Molecular Landscapes in Human Insulinomas," Nature Communications, 8:767 (2017), which is hereby incorporated by reference in its entirety), summarized in Table 2, were remarkable for the abundance of members of the TGFβSF. In addition, harmine treatment of human islets resulted in notable changes in TGFβSF members (Table 3). Reasoning from these observations, from the prominence of SMAD signaling in human insulinoma cell proliferation (Wang et al., "Insights Into Beta Cell Regeneration for Diabetes Via Integration of Molecular Landscapes in Human Insulinomas," Nature Communications, 8:767 (2017), which is hereby incorporated by reference in its entirety), and the beneficial effects of TGFβ signaling inhibition described by others (Mukherjee et al., "FSTL3 Deletion Reveals Roles for TGFbeta Family Ligands in Glucose and Fat Homeostasis in Adults." Proc. Natl. Acad. Sci. 104:1348-53 (2007); Brown and Schneyer, "Emerging Roles for the TGFb Superfamily in Pancreatic Beta Cell Homeostasis," Trends Endocrinol. Metab. 21:441-448 (2010); El-Gohary et al., "A Smad Signaling Network Regulates Islet Proliferation," Diabetes 63:224-36 (2014); Xiao et al., "Transient Suppression of Transforming Growth Factor Beta Receptor Signaling Facilitates Human Islet Transplantation," Endocrinology 157:1348-56 (2016); Xiao et al., "M2 Macrophages Promote Beta Cell Proliferation by Upregulation of SMAD7," Proc. Natl. Acad. Sci. 111:E1211-20 (2014); Smart et al., "Conditional Expression of Smad7 in Pancreatic Beta Cells Disrupts TGF-beta Signaling and Induces Reversible Diabetes Mellitus," PLoS Biology 4:e39 (2006); Zhou et al., "Combined Modulation of Polycomb and Trithorax Genes Rejuvenates Beta Cell Replication," J. Clin. Invest. 123: 4849-58 (2013); and Dhawan et al., "Inhibition of TGF-Beta Signaling Promotes Human Pancreatic Beta Cell Replication," Diabetes 65:1208-18 (2016), which are hereby incorporated by reference in their entirety), the effects of a broad range of pharmacologic TGFβSF inhibitors on human beta cell proliferation in a large number of human cadaveric islet preparations was explored (FIGS. 1A-1B). Vehicle alone (DMSO) had no effect, and harmine displayed its usual 2% labeling index, as assessed using Ki67 labeling of insulin-positive cells. A broad range of TGFβ receptor, BMP receptor, and activin receptor inhibitors had little effect on human beta cell proliferation, as previously reported (Dhawan et al., "Inhibition of TGF-Beta Signaling Promotes Human Pancreatic Beta Cell Replication," *Diabetes* 65:1208-18 (2016), which is hereby incorporated by reference in its entirety). In contrast, every TGFβSF receptor inhibitor tested, whether targeting TGFβ, activin, or BMP receptors, when used in combination with harmine, induced dramatic increases in the Ki67 labeling index in human beta cells. Proliferation rates (labeling indices) averaged in the 5-8% range. However, the large error bars reflect even higher proliferation rates in occasional human islet preparations, sometimes achieving Ki67 labeling indices as high as 15-20%.

Figure 2C:
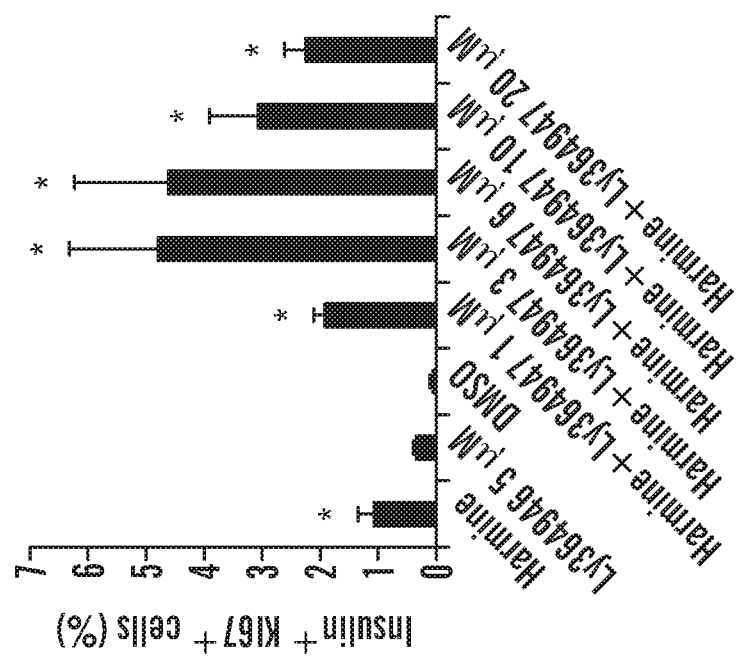
FIGS. 2A-2G show the induction of proliferation with combination therapy with other harmine analogues; confirmation with BrdU and PHH3; and demonstration of synergistic interactions.
Figure 2B:
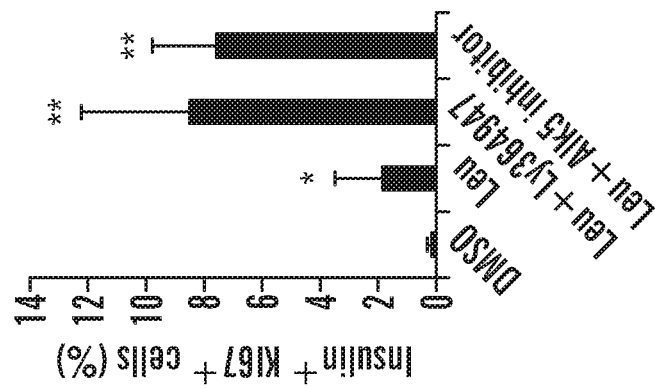
Figure 2A:
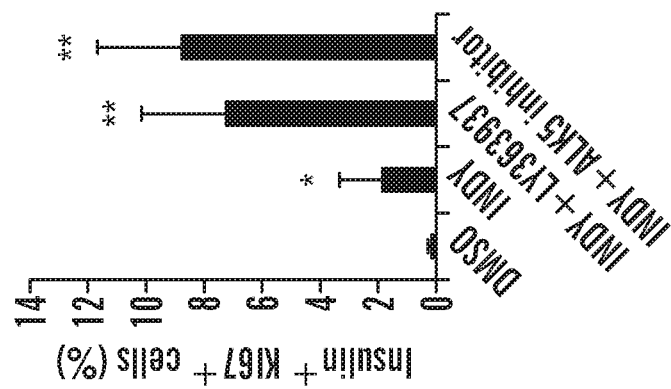
Figure 2D:
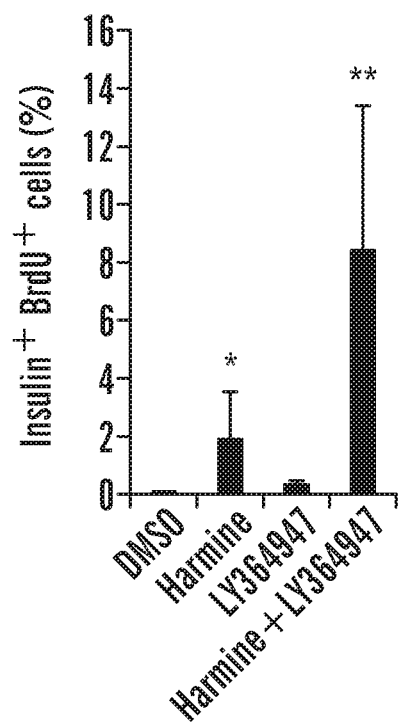
Figure 2E:
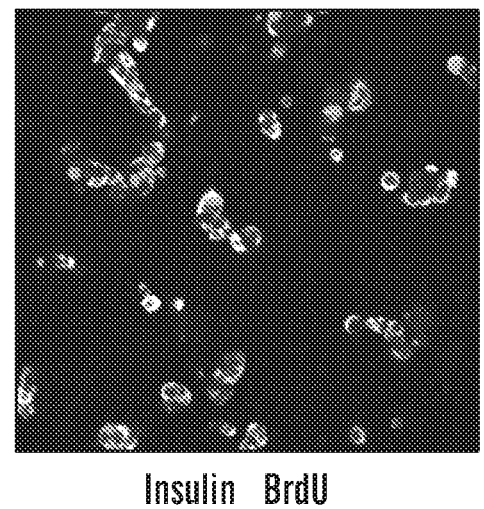
Figure 2F:
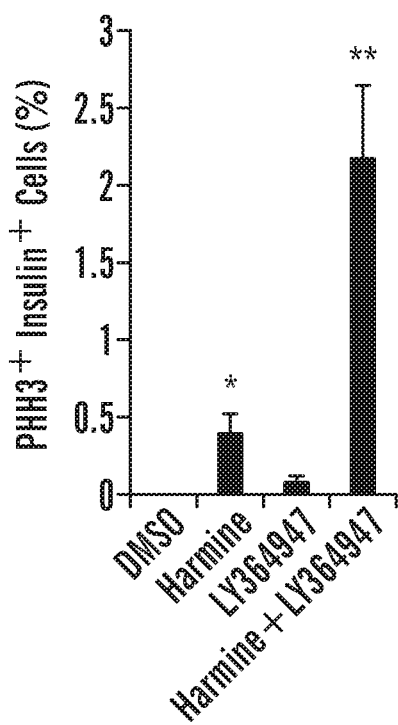
Figure 2G:
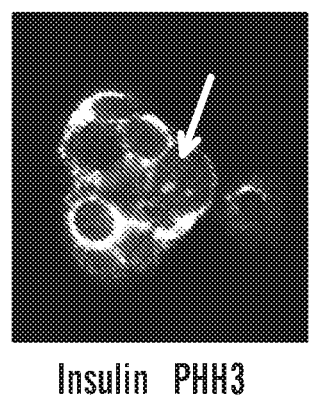

The beneficial effects were not confined to harmine, but extended to additional DYRK1A inhibitors, including INDY and leucettine-41 (Tahtouh et al., "Selectivity, Co-Crystal Structures and Neuroprotective Properties of Leucettines, a Family of Protein Kinase Inhibitors Derived from the Marine Sponge Alkaloid Leucettamine B," *J. Med. Chem.* 55:9312-30 (2012), which is hereby incorporated by reference in its entirety) (FIGS. 2A-2B). In addition, in dose-response studies, the combinations fulfilled formal criteria for pharmacologic synergy (FIG. 2C). Further, the remarkable synergy could be observed with two additional measures of proliferation: BrdU incorporation and phospho-histone-3 immunolabeling (FIGS. 2D-2G).

Figure 3E:
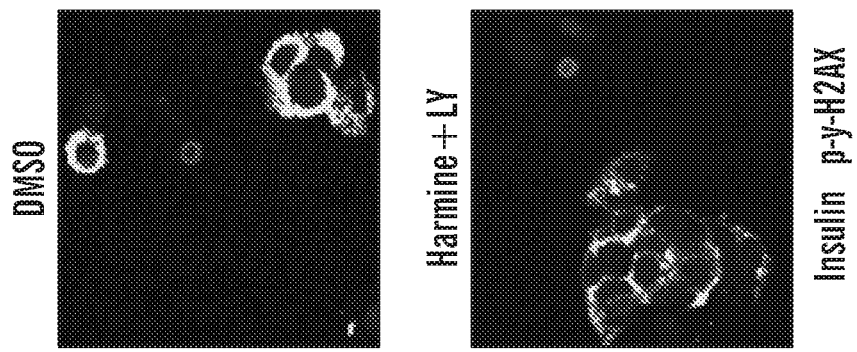
Figure 3D:
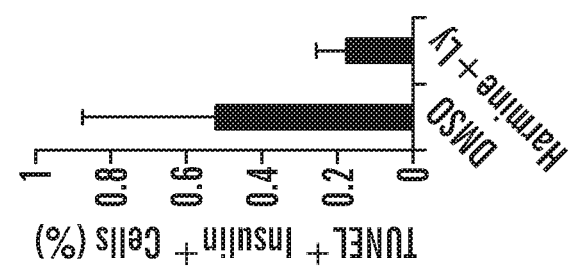
Figure 3C:
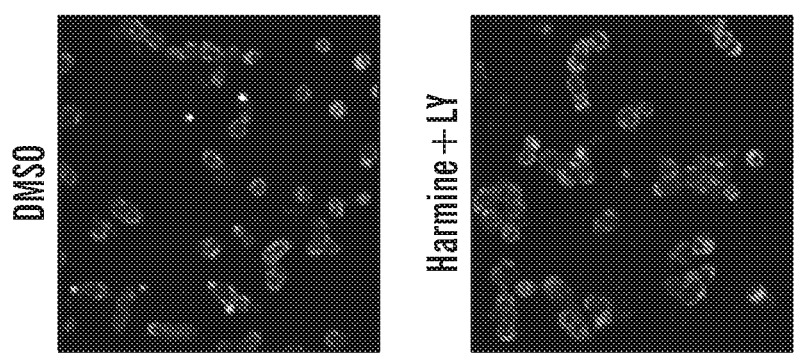

The mitogenic effects of the combination were not observed to be specific to beta cells: proliferation was observed in alpha, delta, PP, and ductal cells as well (FIGS. 3A-3B). No adverse effects were observed with respect to beta cell death or DNA damage as assessed by TUNEL assay and γH2AX immunolabeling, respectively (FIGS. 3C-3E).

Figure 4A:
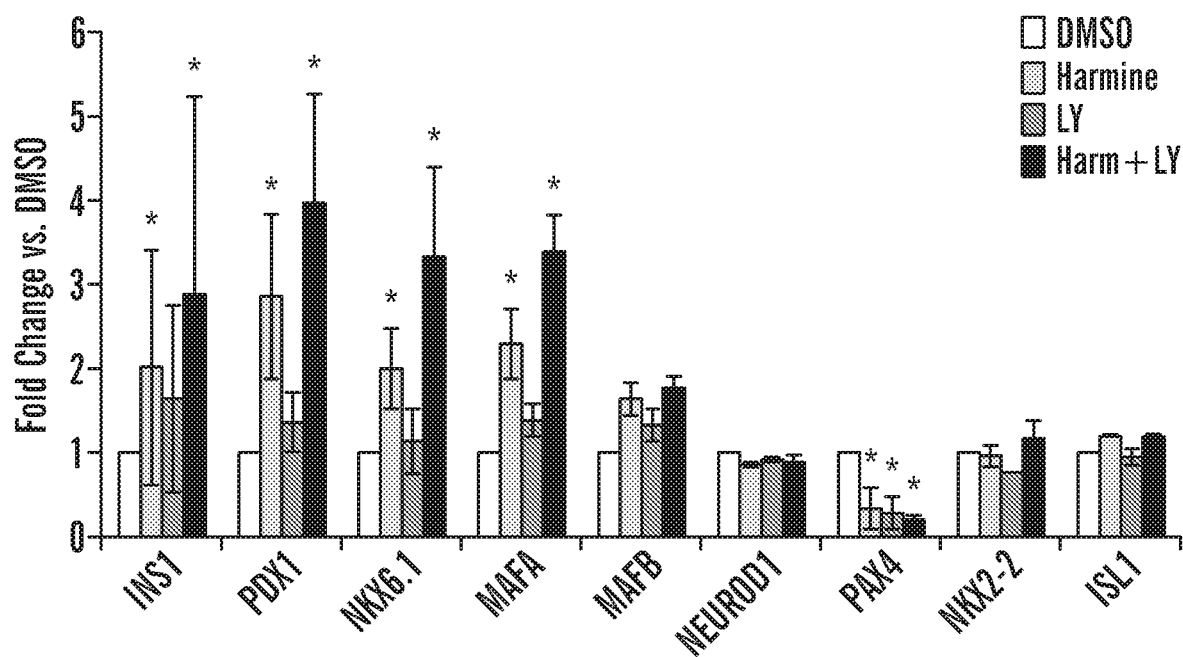
FIGS. 4A-4F show that the harmine-TGFβSF inhibition combination increases beta cell transcription factors.
Figure 4B:
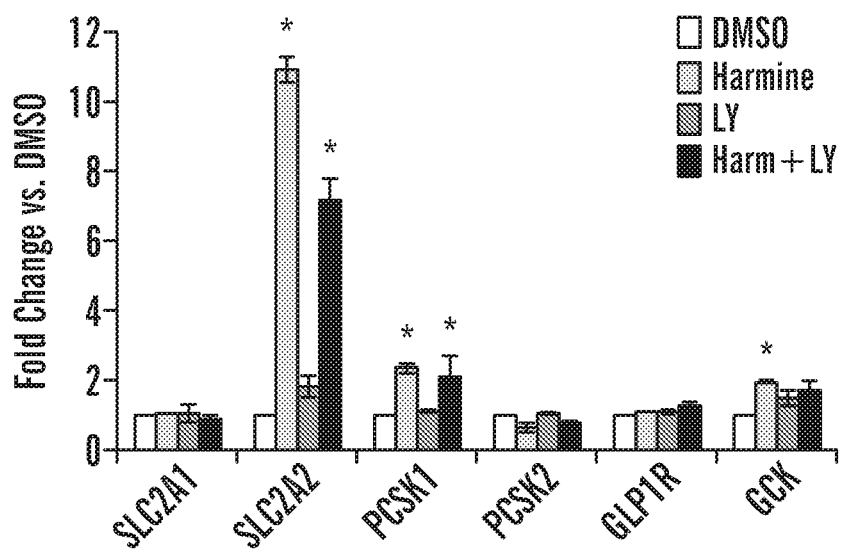
Figures 4C, 4D:
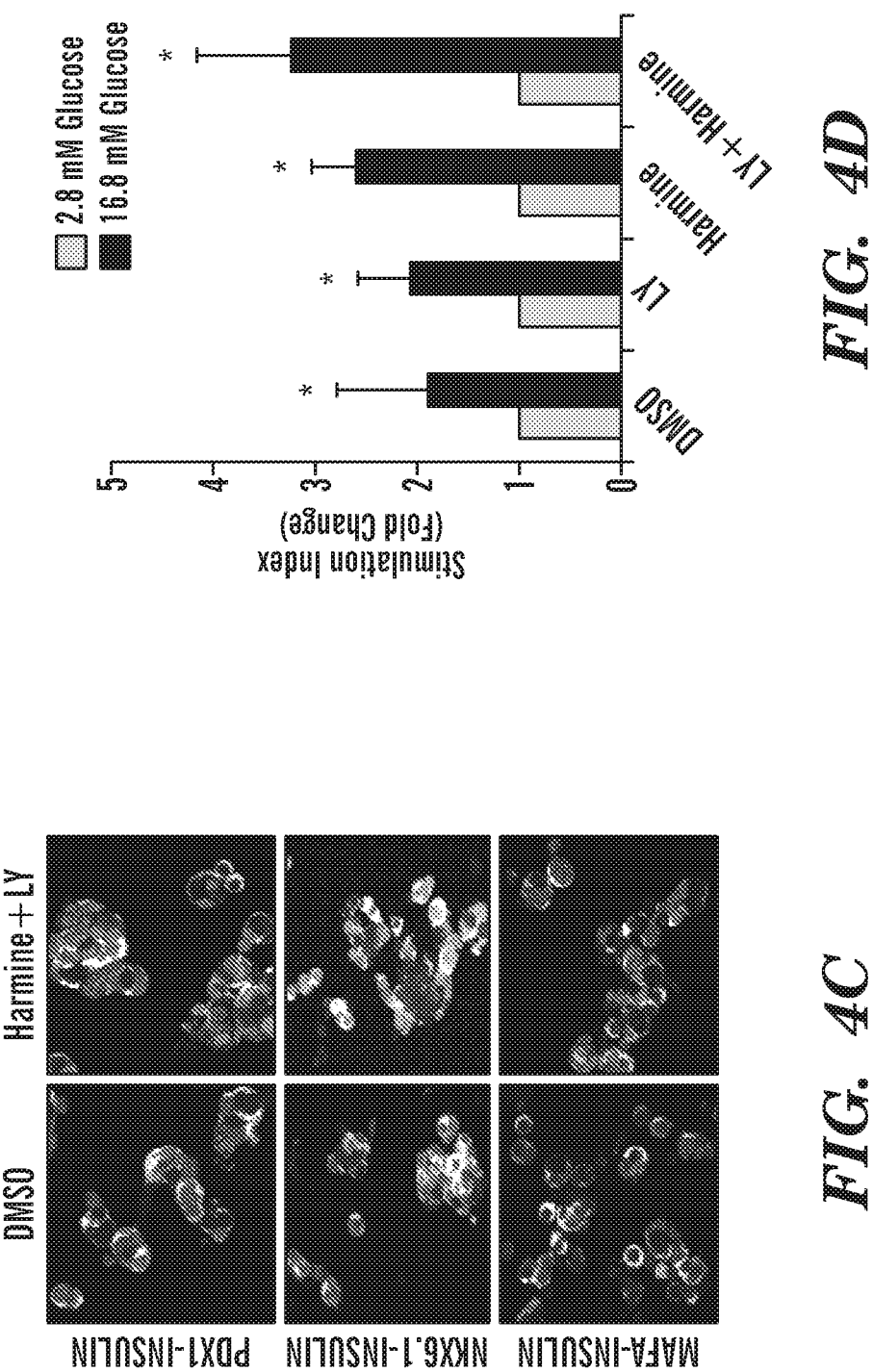

Example 2—Harmine-TGKβSF Combinations Enhance Markers of Human Beta Cell Differentiation in Normal and Type 2 Diabetes Islets Concerned that activation of mitogenic pathways might lead to de-differentiation of beta cells, gene expression of a panel of markers of beta cell differentiation was explored (FIGS. 4A-4B). As observed for harmine alone (Wang et al., "A High-Throughput Chemical Screen Reveals That Harmine-Mediated Inhibition of DYRK1A Increases Human Pancreatic Beta Cell Replication," *Nature Medicine* 21:383-388 (2015), which is hereby incorporated by reference in its entirety), the harmine-TGFβSF inhibitor combination not only failed to induce de-differentiation, the opposite occurred: gene expression of key beta cell markers such as INS (insulin), PDX1, NKX6.1, MAFA, MAFB, SLC2A2, and PCSK1(FIGS. 4A-4B) all increased with combined harmine-TGFβSF inhibitor treatment, as assessed on whole islets by qPCR. Gene expression of ISL1, SLC2A1, NeuroD, NKX2.2, and PCSK2 all remained the same as at baseline (FIGS. 4A-4B). Only PAX4 declined, the significance of which is uncertain. These results were confirmed by immunocytochemistry in dispersed human islet preparations, which revealed that PDX1, NKX6.1, and MAFA were all increased specifically in human beta cells (FIG. 4C). In line with these observations, glucose-stimulated insulin secretion was normal, and possibly accentuated in human islets treated with the harmine-TGFβSF inhibitor combination (FIG. 4D).

Figure 4F:
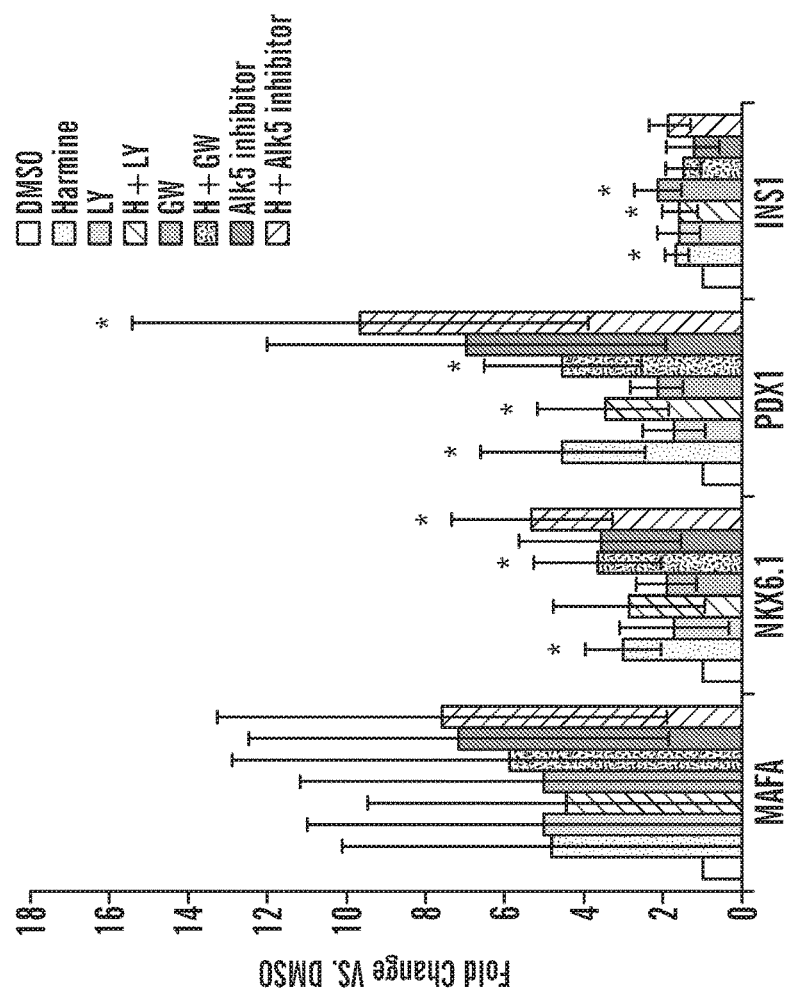
Figure 4E:
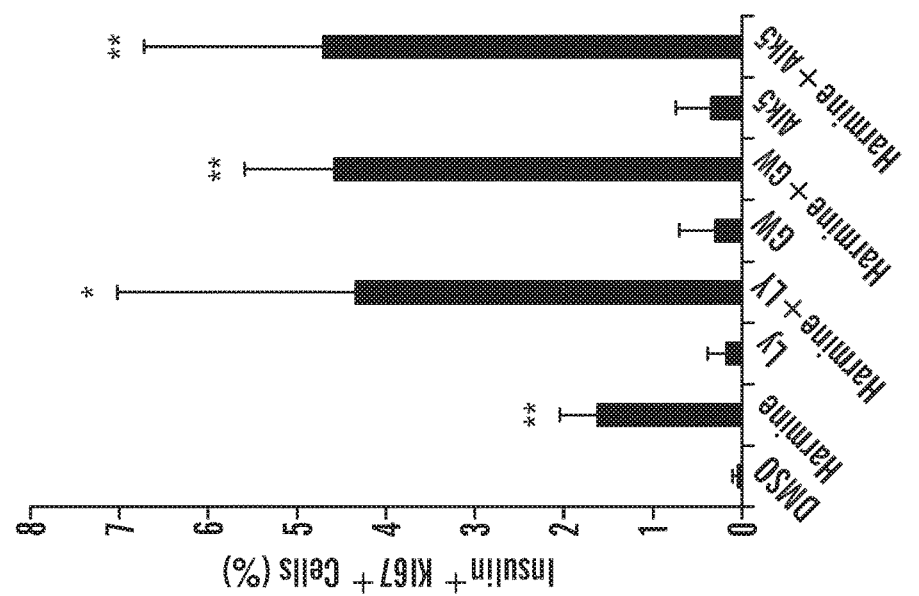

Since de-differentiation of beta cells occurs in islets from mice and people with T2D (Talchai et al., "Pancreatic Beta Cell Dedifferentiation as a Mechanism of Diabetic Beta Cell Failure," *Cell* 150:1223-34 (2012) and Cinti et al., "Evidence of Beta Cell Dedifferentiation in Human Type 2 Diabetes," *J. Clin. Endocrinol. Metab.* 101:1044-54 (2016), which are hereby incorporated by reference in their entirety), proliferation in islets derived from donors with Type II diabetes was next explored (FIG. 4E). Remarkably, harmine alone increased Ki67 immunolabeling to the same degree observed in non-diabetic islet donors; moreover, harmine in combination with three different TGFβSF inhibitors led to synergistic increases in Ki67 labeling comparable to that observed in normal islets (FIGS. 1A-B and FIGS. 2A-G). Equally remarkably, multiple harmine-TGFβSF inhibitor combinations led to marked increases in expression of key beta cell markers PDX1, NKX6.1, and MAFA. This was associated with significant increases in human T2D islet insulin gene expression (FIG. 4F).

Example 3—Combined Efficacy Requires SMAD and DYRK1A Signaling

Figure 5C:
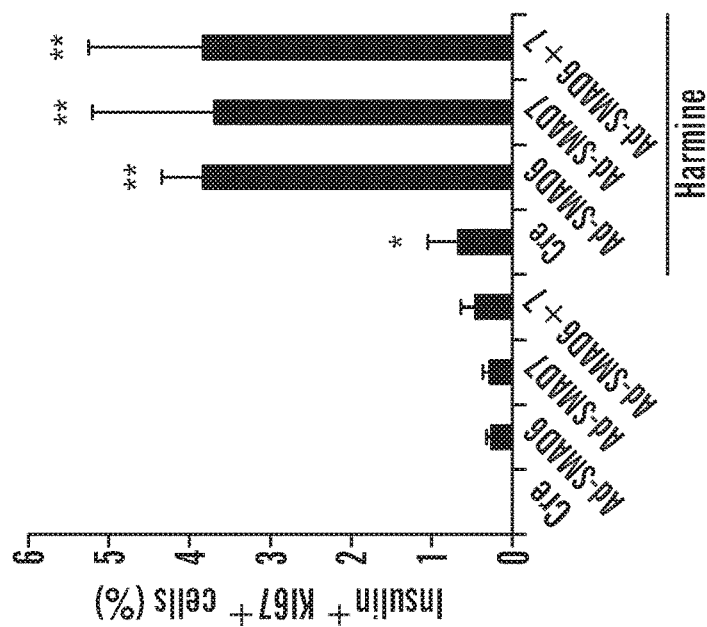
FIGS. 5A-5G show the requirements for DYRK1A and SMAD signaling.
Figure 5B:
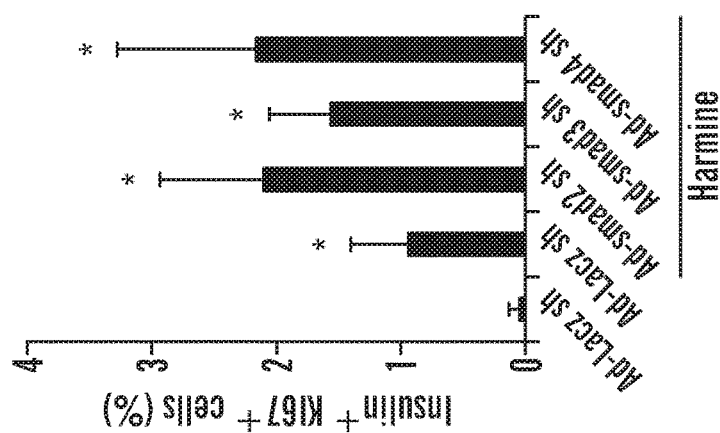
Figure 5A:
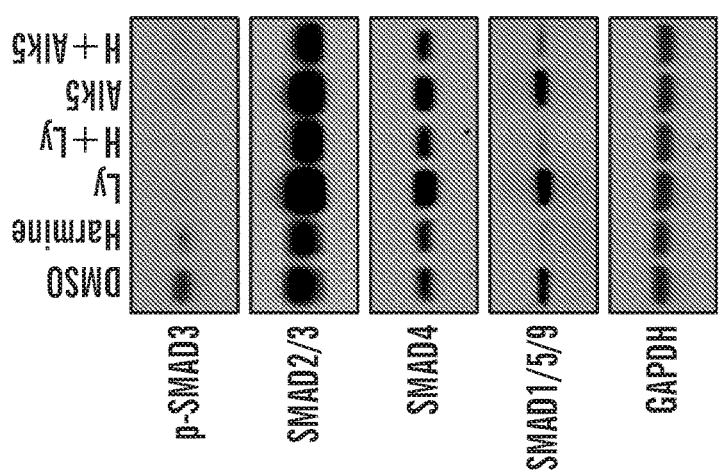

TGFβSF ligands affect SMAD signaling but may also recruit other signaling pathways (Brown and Schneyer, "Emerging Roles for the TGFb Superfamily in Pancreatic Beta Cell Homeostasis," *Trends Endocrinol. Metab.* 21:441-448 (2010); Stewart et al., "Human Beta Cell Proliferation and Intracellular Signaling: Part 3," *Diabetes* 54:1872-85 (2015); Macias et al., "Structural Determinants of Smad Function in TGF-Beta Signaling," *Trends Biochem. Sci.* 40:296-308 (2015); and Gaarenstroom & Hill, "TGF-Beta Signaling to Chromatin: How Smads Regulate Transcription," *Seminars Cell Devel. Biol.* 32:107-118 (2014), which are hereby incorporated by reference in their entirety). To ascertain whether the harmine-TGFβSF inhibitor combination affected SMAD signaling, human islets were incubated with harmine alone or in combination with two TGFβSF inhibitors: LY or ALK5 (FIG. 5A). The harmine-TGFβSF inhibitor combinations led to reductions in SMAD3 phosphorylation without altering SMAD2/3 abundance, and also led to dramatic reductions in total SMADs 1/5/9 (note that antisera cannot distinguish between these three SMADs). Perhaps most interestingly, harmine alone led to reductions in phospho-SMAD3 as well as to reductions in total SMAD1/5/9. To explore the requirement for SMAD signaling in the proliferation induced by the harmine-TGFβSF inhibitor combinations, R-SMADs 2, 3, and 4 were adenovirally silenced in human islets treated with harmine (FIGS. 5B-5C), and observed that silencing these three R-SMADs further enhanced harmine-induced human beta cell proliferation. Conversely, overexpressing the I-SMADs 6 and 7 had no effect on proliferation by themselves, but markedly enhanced harmine-induced proliferation. Collectively these results reveal three key points. First, the proliferation generated by the TGFβSF inhibitors when given in combination with harmine is mediated entirely or in large part via SMAD signaling: silencing R-SMADs or overexpressing I-SMADS can substitute for TGFβSF inhibitors in the combination. Second, harmine itself has previously unrecognized inhibitory effects in SMAD signaling. Third, multiple SMAD families (i.e., both the canonical TGFβ receptor-associated SMADs 2, 3, and 4 as well as the canonical BMP receptor-associated SMADs 1, 5, and 8/9 are able to modulate harmine-mediated proliferation.

Figure 5E:
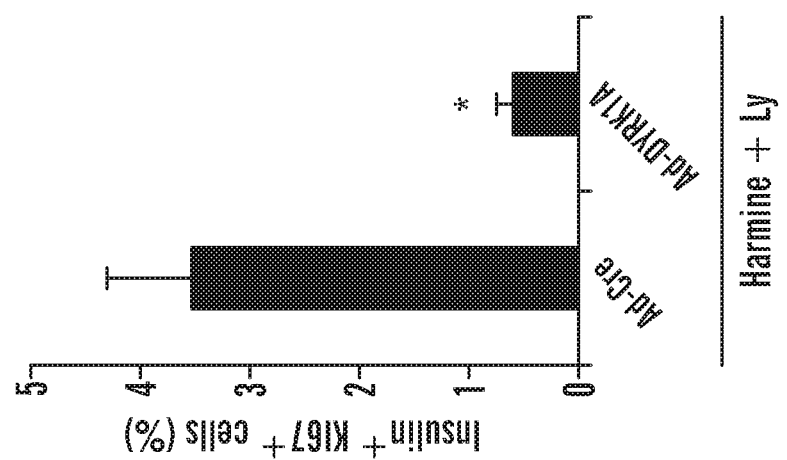
Figure 5D:
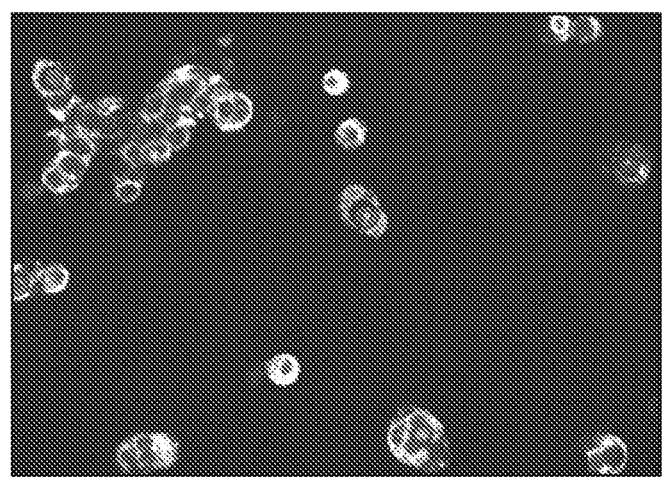
Figure 5G:
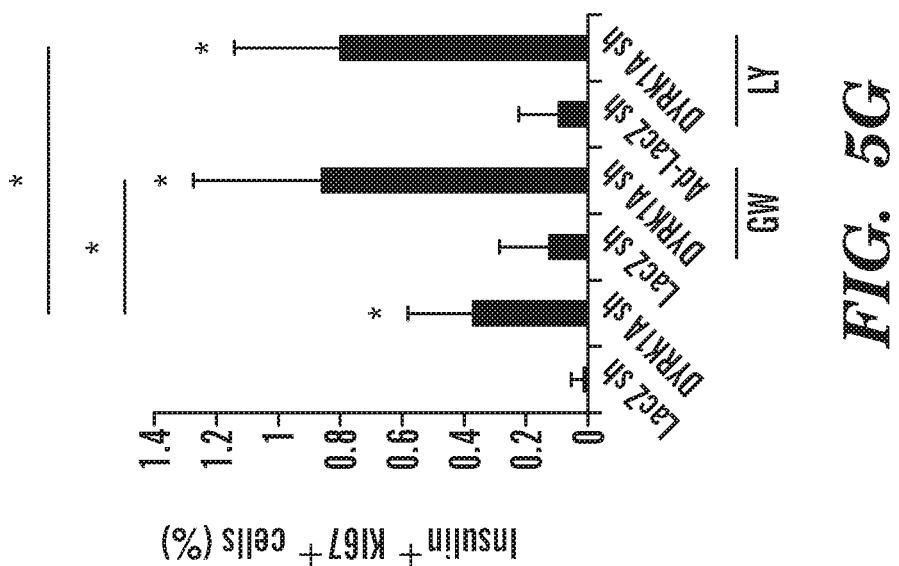
Figure 5F:
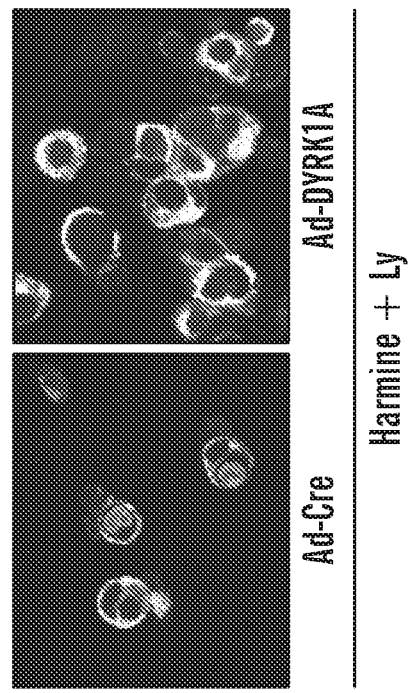

Harmine analogues derive their mitogenic effects in large part if not exclusively via inhibition of DYRK1A (Wang et al., "A High-Throughput Chemical Screen Reveals that Harmine-Mediated Inhibition of DYRK1A Increases Human Pancreatic Beta Cell Replication," *Nature Med.* 21:383-388 (2015); Shen et al., "Inhibition of DYRK1A and GSK3B Induces Human Beta Cell Proliferation," *Nature Comm.* 6:8372 (2015); and Dirice et al., "Inhibition of DYRK1A Stimulates Human Beta Cell Proliferation," *Diabetes* 65:1660-71 (2016), which are hereby incorporated by reference in their entirety). To explore the presumed requirement for DYRK1A in the synergistic proliferation derived from the harmine-TGFβ inhibitor combination, adenoviral overexpression and silencing of DYRK1A alone or in combination with TGFβSF inhibition was employed (FIGS. 5E-5G). These experiments reveal that DYRK1A overexpression is able to block proliferative effects of the harmine-TGFβ inhibitor combination, and conversely, that DYRK1A loss markedly accentuates proliferation induced by the TGFβ inhibitors GW and LY. Collectively, the results in FIGS. 5A-5G illustrate that the majority, if not all, of the accentuated effects of the harmine-TGFβ inhibitor combination on human beta cell proliferation are attributable to combined interruption of both DYRK1A and SMAD signaling. They also reveal that harmine can have unanticipated direct or indirect effects to reduce R-SMAD signaling.

Figure 6A:
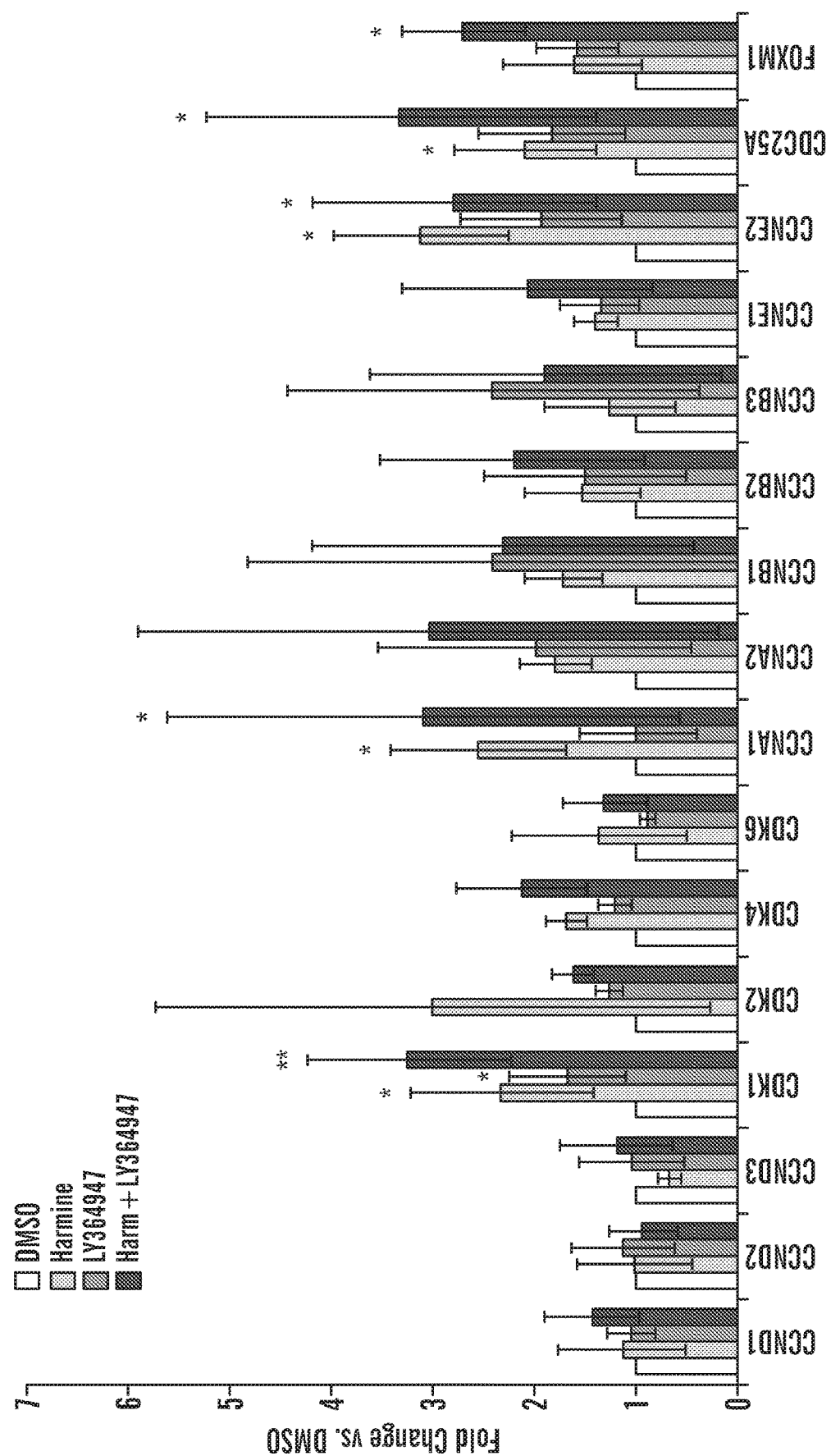
Figure 6B:
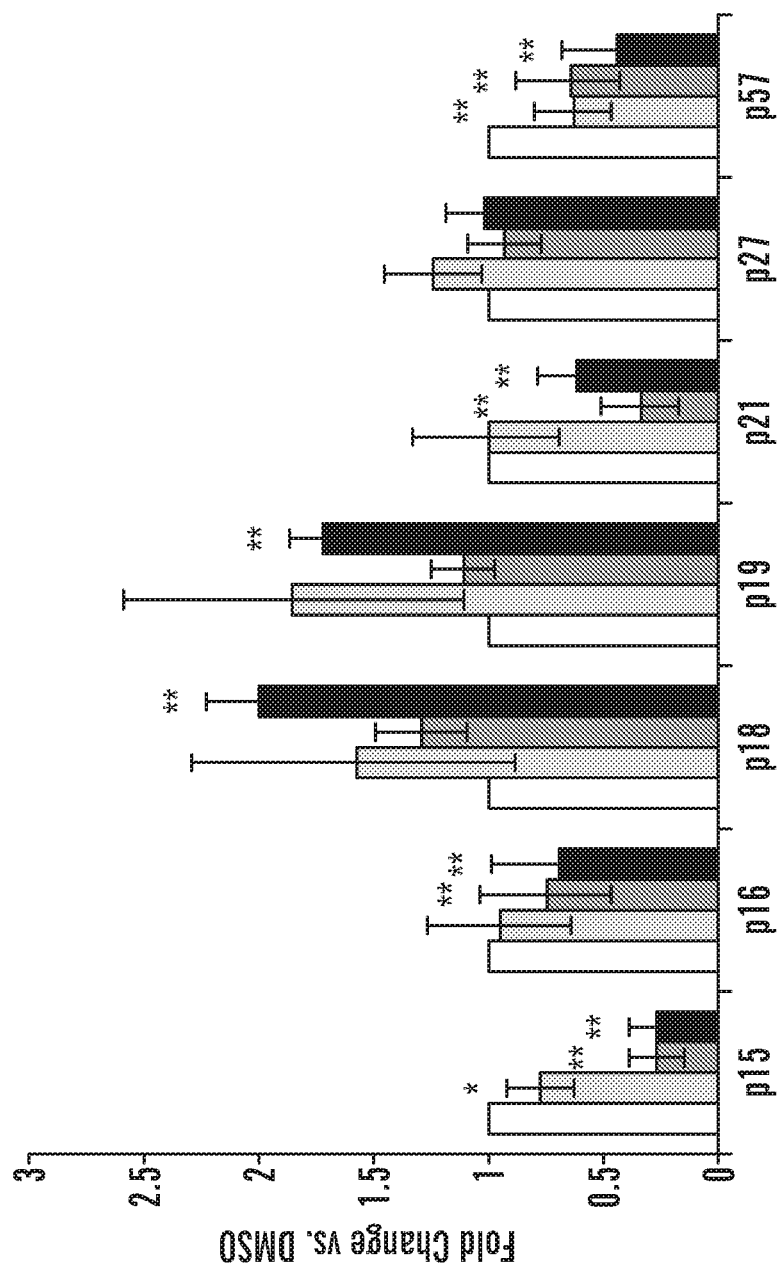

Example 4—The Harmine-TGFβSF Inhibitor Synergy Reflects Complimentary Effects on Cyclins/CDKs and CDK Inhibitors Reasoning that harmine and harmine-TGFβ inhibitors (and DYRK1A and SMADs, respectively) must ultimately orchestrate cell cycle entry via cell cycle activators and cell cycle inhibitors, gene expression of cell cycle activators and inhibitors was examined in whole islets treated with vehicle, harmine, TGFβ inhibitor or the harmine-TGFβ inhibitor combination (FIGS. 6A-6B). Harmine alone, as described previously (Wang et al., "A High-Throughput Chemical Screen Reveals That Harmine-Mediated Inhibition of DYRK1A Increases Human Pancreatic Beta Cell Replication," *Nature Medicine* 21:383-388 (2015), which is hereby incorporated by reference in its entirety), induced expression of a number of cell cycle activators (e.g., CDK1, CCNA1, CCNE2, and CDC25A). In contrast, the TGFβ inhibition alone had little effect. Notably, the harmine-TGFβ inhibitor combination induced no further activation of these or other cyclins or cdks: the harmine-TGFβ inhibitor combination was equivalent to harmine alone.

Figure 6E:
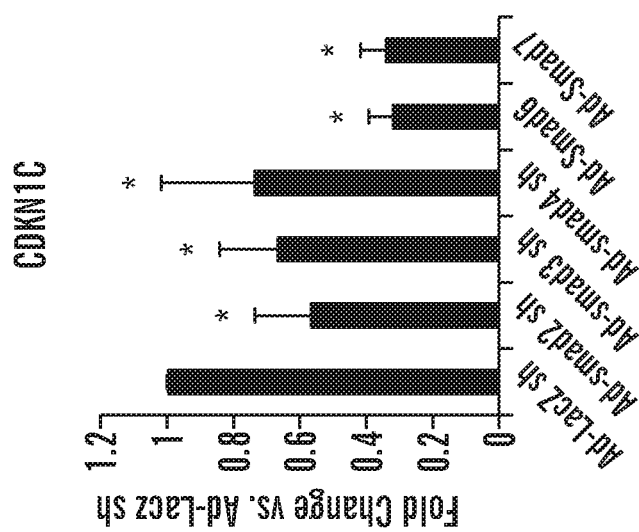
Figure 6D:
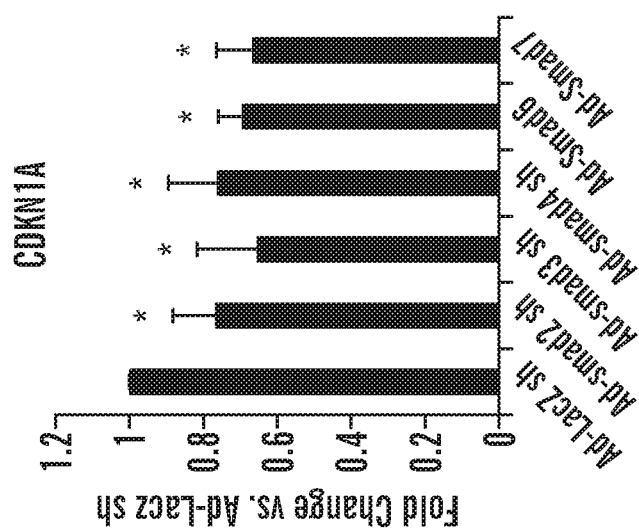
Figure 6C:
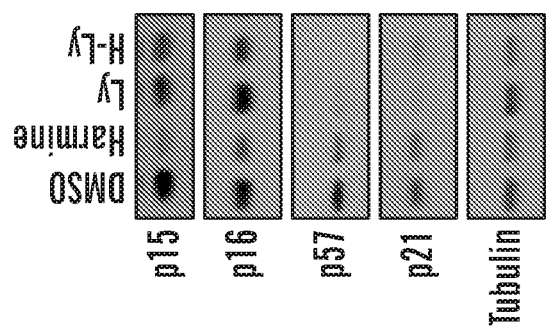

On the other hand, cell cycle inhibitors behaved differently (FIGS. 6B-6C). Harmine alone had modest and limited effects on cell cycle inhibitor expression, with the exception of CDKN1C (encoding p57$^{KIP2}$) which declined by ~50%. TGFβ inhibition reduced expression of CDKN2B (encoding p15$^{INK4b}$), CDKN1A (encoding p21$^{CIP}$), and CDKN1C/p57$^{KIP2}$. Remarkably, the harmine-TGFβ inhibitor combination induced marked reductions in three key cell cycle inhibitors, CDKN2B, CDKN1A, and CDKN1C.

To explore the mechanism underlying the decline in CDKN1A, CDKN1C, and CDKN2B in response to TGFβ inhibition, the effects of adenovirally silencing R-SMADs 2, 3, and 4, or overexpressing I-SMADs 6 and 7 on CDKN1A, CDKN1C, and CDKN2B expression in human islets were investigated. Silencing the R-SMADs or overexpressing I-SMADs reduced CDKN1A and CDKN1C expression (FIGS. 6D-6E), but had little effect on CDKN2B expression. To determine whether CDKN1A and/or CDKN1C reductions might underlie the synergistic effects of the TGFβSF inhibition in the harmine-TGFβSF inhibitor combination, CDKN1A and CDKN1C were silenced in human islets, either alone or in combination with harmine treatment (FIG. 6F). As reported previously (Wang et al., "Insights Into Beta Cell Regeneration for Diabetes Via Integration of Molecular Landscapes in Human Insulinomas," *Nature Communications,* 8:767 (2017) and Avrahami et al., "Targeting the Cell Cycle Inhibitor p57Kip2 Promotes Adult Human Beta Cell Replication," *J. Clin. Invest.* 124:670-674 (2014), which are hereby incorporated by reference in their entirety), CDKN1C silencing led to a modest increase in human beta cell proliferation, and silencing CDKN1A had no effect. In contrast, in the presence of harmine, silencing of either or both CDKN1A or CDKN1C led to robust human beta cell proliferation. Finally, to determine whether CDKN1A, CDKN1C, and CDKN2B truly function as cell cycle inhibitors in human beta cells, these were overexpressed in human islets treated with harmine and the TGFβ inhibitor LY364947. Each cell cycle inhibitor dramatically reduced proliferation in harmine-TGFβ inhibitor treated human beta cells to "rates" approaching zero.

Collectively, these observations suggest a mechanism for the synergistic effects of the harmine-TGFβ inhibitor combination on proliferation: harmine, through DKRK1A inhibition and nuclear NFAT retention (Wang et al., "A High-Throughput Chemical Screen Reveals That Harmine-Mediated Inhibition of DYRK1A Increases Human Pancreatic Beta Cell Replication," *Nature Medicine* 21:383-388 (2015); Heit et al., "Calcineurin/NFAT Signaling Regulates Pancreatic β-Cell Growth and Function," *Nature* 443:345-349 (2006); Goodyer et al., "Neonatal Beta Cell Development in Mice and Humans is Regulated by Calcineurin/NFaT," *Developmental Cell* 23:21-34 (2012); and Demozay et al., "Specific Glucose-Induced Control of Insulin Receptor-Supstrate-2 Expression is Mediated by Ca$^{2+}$-Dependent Calcineurin-NFAT Signaling in Primary Pancreatic Islet β-Cells," *Diabetes* 60:2892-2902 (2011), which are hereby incorporated by reference in their entirety), predominantly activates cell cycle genes in a complimentary fashion, TGFβ inhibition, via attenuation of SMAD signaling, reduces expression of CDKN2B, CDKN1A, and CDKN1C, each of which normally functions as a cell cycle inhibitor in human beta cells. This TGFβ inhibitor-mediated reduction in CDKN2B, CDKN1A, and CDKN1C, compliments with harmine-induced, DYRK1A-NFaT mediated increases in cyclins and CDKs, permitting greater cell cycle activation than occurs via harmine treatment or TGFβ inhibition alone.

Example 5—Direct Effects of R-SMADs and Trithorax Complex on Cell Cycle Inhibitors R-SMADs may transactivate or repress genes, and may do so in complexes that include Trithorax members (Zhou et al., "Combined Modulation of Polycomb and Trithorax Genes Rejuvenates Beta Cell Replication," *J. Clin. Invest.* 123:4849-58 (2013); Dhawan et al., "Inhibition of TGF-Beta Signaling Promotes Human Pancreatic Beta Cell Replication," *Diabetes* 65:1208-18 (2016); Stewart et al., "Human Beta Cell Proliferation and Intracellular Signaling: Part 3,*"* *Diabetes* 54:1872-85 (2015); Macias et al., "Structural Determinants of Smad Function in TGF-Beta Signaling," *Trends Biochem. Sci.* 40:296-308 (2015); and Gaarenstroom & Hill, "TGF-Beta Signaling to Chromatin: How Smads Regulate Transcription," *Seminars Cell Devel. Biol.* 32:107-118 (2014), which are hereby incorporated by reference in their entirety), both of which have been implicated in beta cell proliferation in human insulinoma (Wang et al., "Insights Into Beta Cell Regeneration for Diabetes Via Integration of Molecular Landscapes in Human Insulinomas," *Nature Communications,* 8:767 (2017), which is hereby incorporated by reference in its entirety). Thus, whether R-SMADS 2, 3, and/or 4 might associate with regulatory regions of the CDKN1A and/or CDKN1C genes in human islets was next investigated (FIGS. 7A-7F).

Figure 7A:
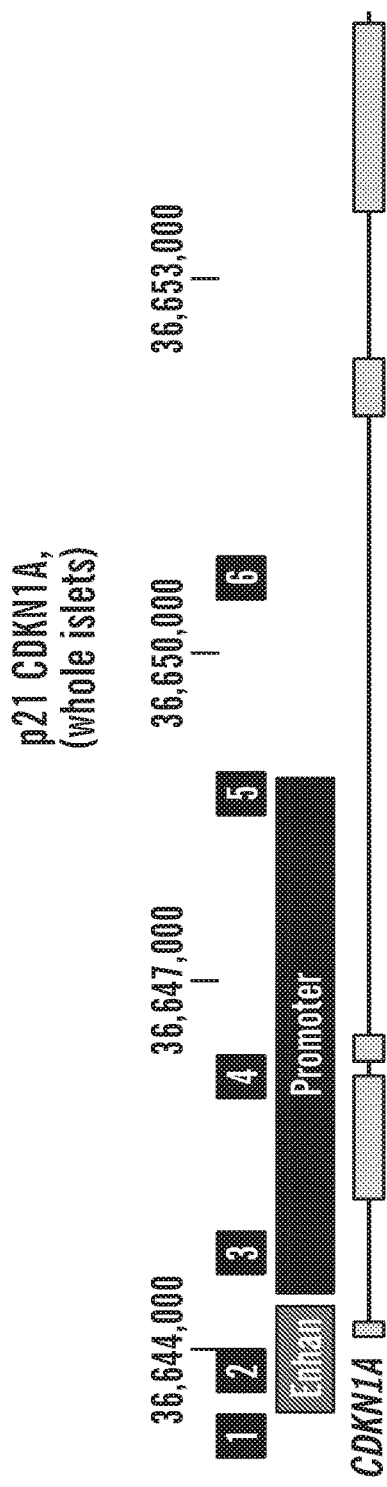
FIGS. 7A-7F show the direct interaction of SMADs and Trithorax members with the CDKN1A and CDKN1C loci in human islets.
Figure 7B:
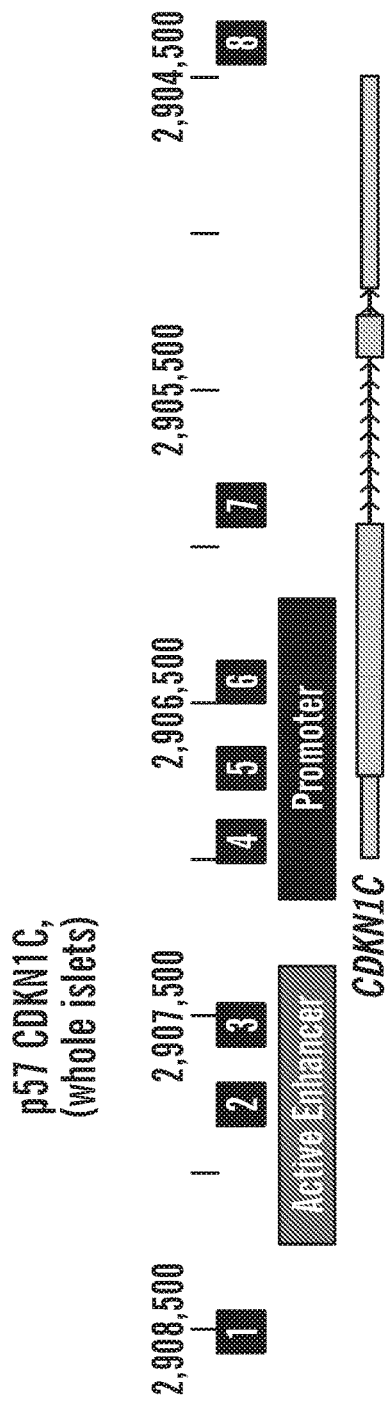
Figure 7C:
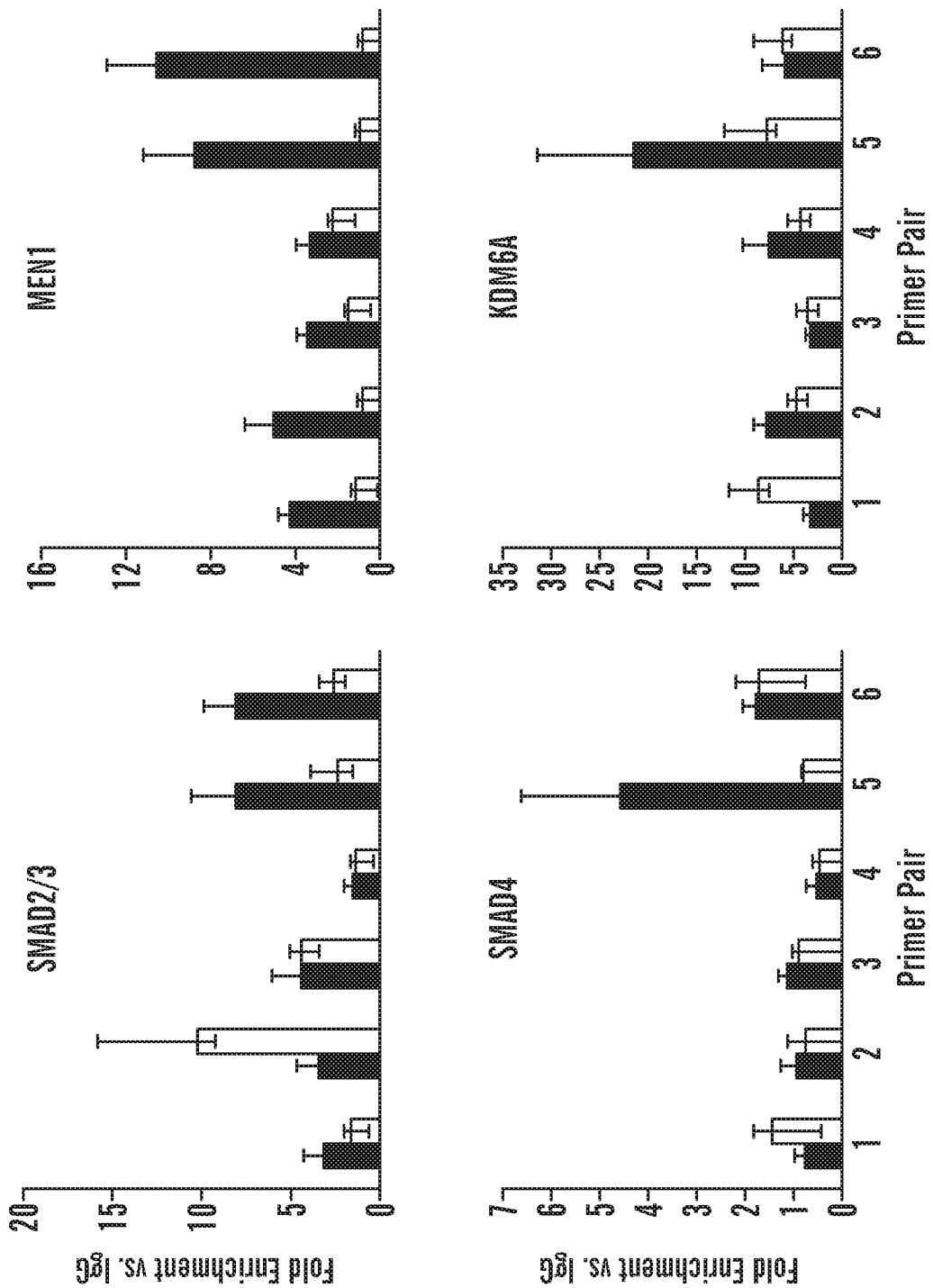
Figure 7D:
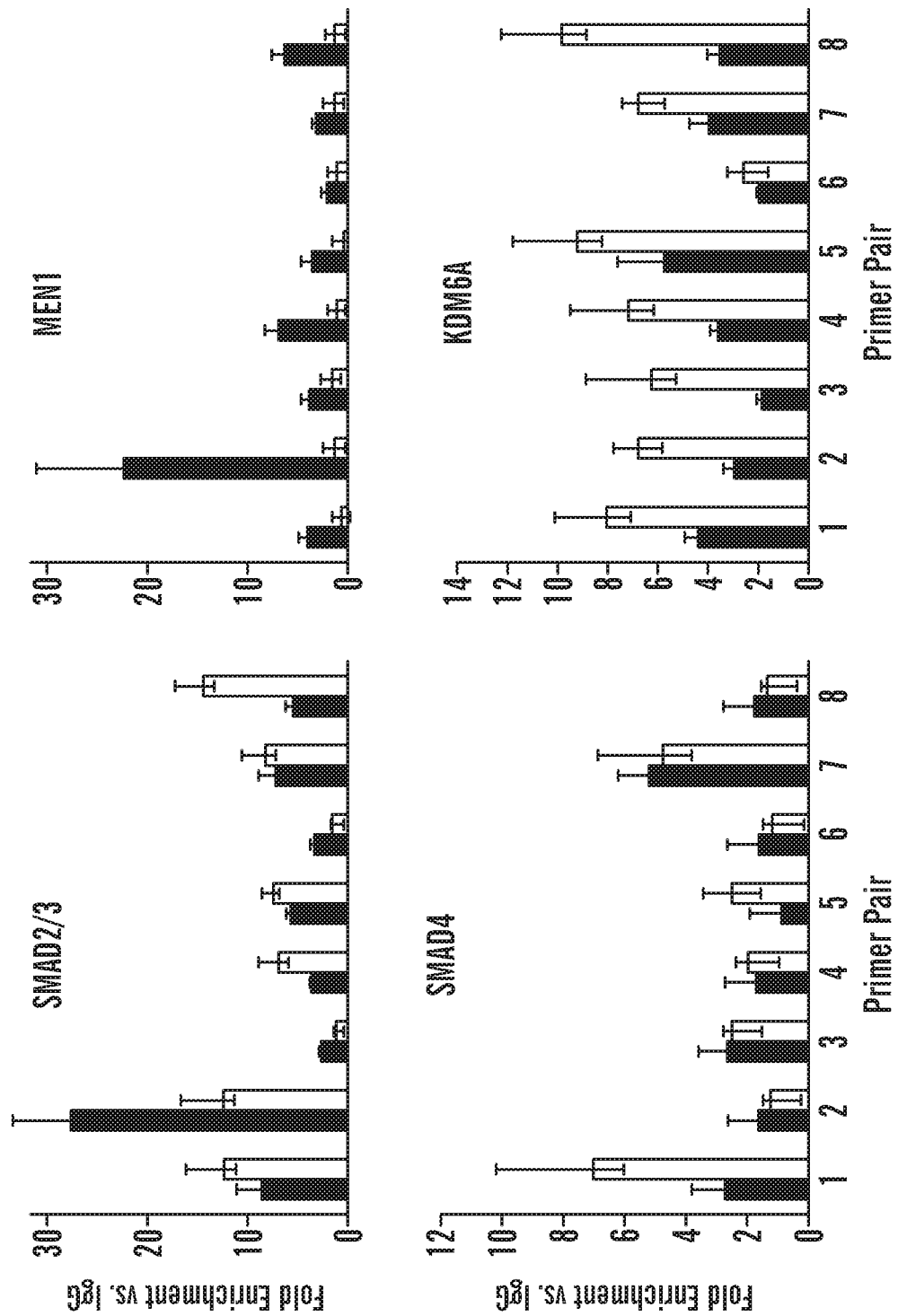
Figure 7E:
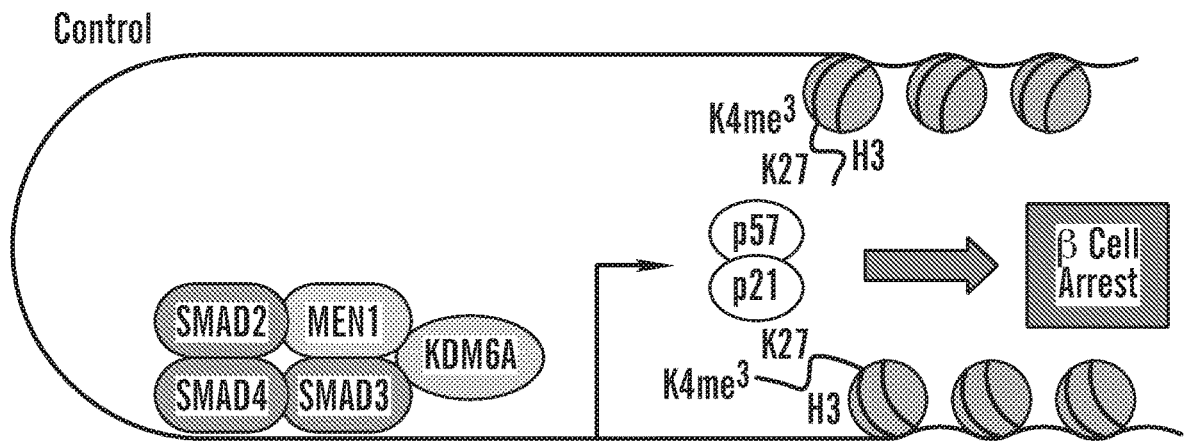
Figure 7F:
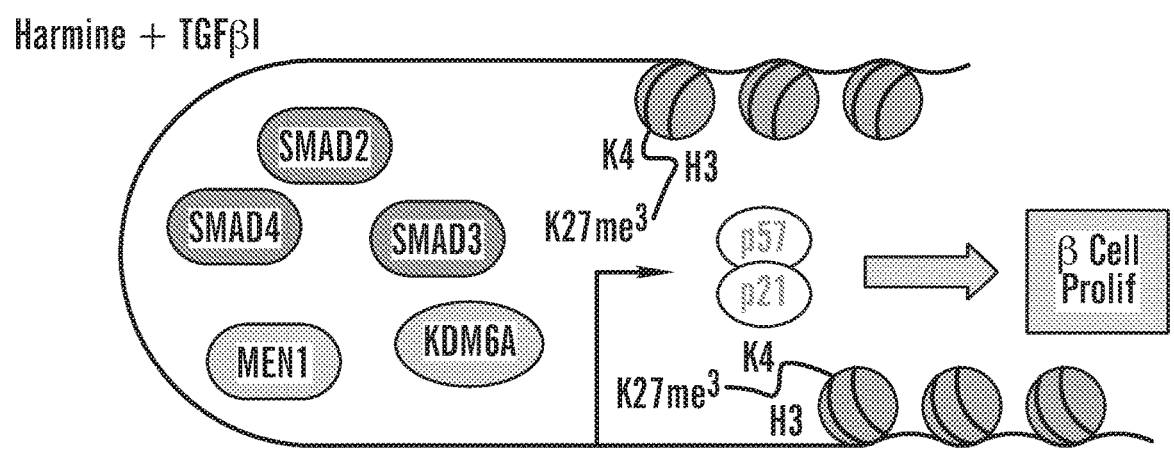

Indeed, SMADs 2/3 and 4 associate with promoter and enhancer regions of CDKN1A and CDKN1C (black bars in FIG. 7C), and these associations are diminished by treatment with the harmine-TGFβ inhibitor combination. Notably, MEN1, a trithorax member and H3K4 methylase, was also observed to bind to these same regions of both CDKN1A and CDKN1C, and this association was also dramatically diminished by harmine-TGFβ inhibitor treatment. Finally, the H3K27 demethylase, KDM6A, is also a Trithorax member, that binds specifically to the CDKN1C promoter in FACS-sorted human beta cells (Wang et al., "Insights Into Beta Cell Regeneration for Diabetes Via Integration of Molecular Landscapes in Human Insulinomas," *Nature Communications*, 8:767 (2017), which is hereby incorporated by reference in its entirety). KDM6A co-localizes with MEN1 on the CDKN1A promoter in human islets, and this association is diminished by harmine-TGFβ inhibitor treatment (FIG. 7C). Paradoxically, in contrast to results with MEN1, while the KDM6A associates with the CDKN1C locus in human islets, this association appears to be enhanced rather than reduced with harmine-TGFβ inhibitor treatment. Taken together, these observations make it clear that R-SMADs, MEN1, and KDM6A, do indeed directly bind to the regulatory regions of CDKN1A and CDKN1C in human beta cells, and do so at loci also occupied by Trithorax members. Importantly, these associations are disrupted by harmine-TGFβ inhibitor treatment. These observations suggest a model (FIGS. 7E-7F) in which SMAD-Trithorax interactions maintain CDKN1A and CDKN1C expression in beta cells under basal circumstances, under the influence of TGFβSF-mediated SMAD signaling in coordination with a Trithorax-mediated open chromatin state at these loci. With harmine-TGFβ inhibitor treatment, these complexes dissociate, permitting loss of SMAD-transactivation chromatin compaction in the CDKN1A and CDKN1C loci.

Figure 9B:
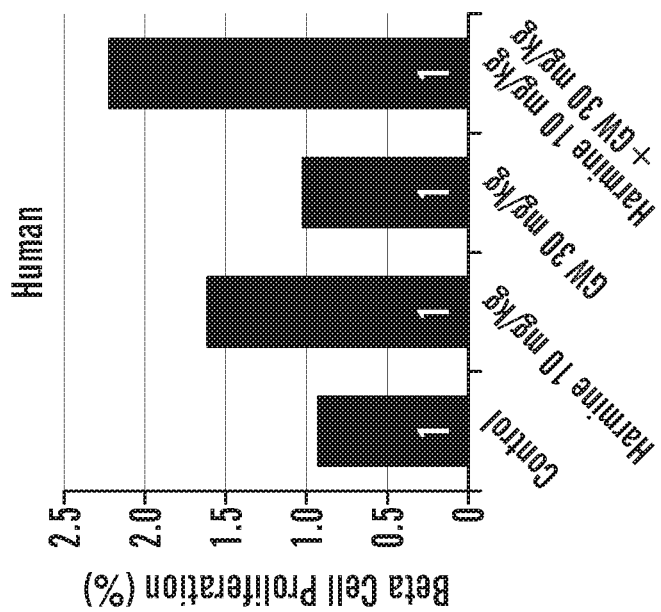
FIGS. 9A-9B show the efficacy of the harmine-TGFβSF1 combination on mouse and human beta cell proliferation in vivo.
Figure 9A:
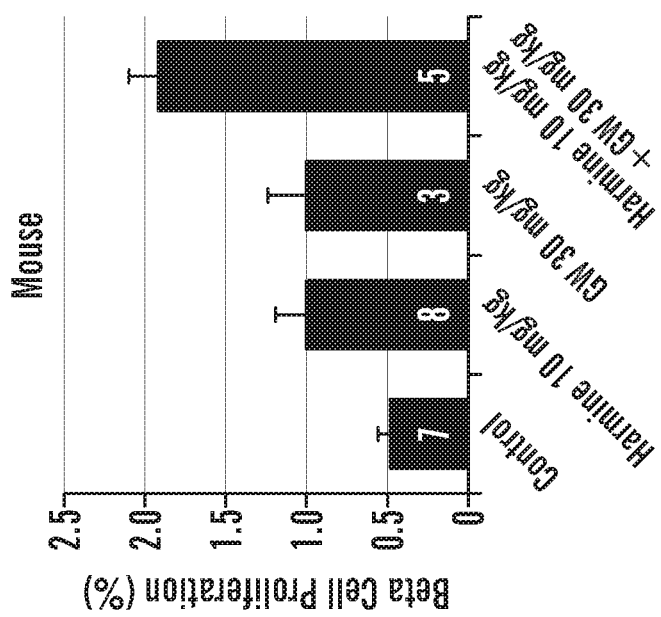

Example 6—Harmine-TGFβ Inhibitor Treatment Enhances Mouse and Human Beta Cell Proliferation In Vivo To evaluate the effects of harmine and TGFβ inhibitor in vivo, C57BL6N mice were administered vehicle (DMSO), harmine, GW788388, or the combination of harmine plus GW788388 intraperitoneally for seven days, sacrificed, and evaluated for insulin and Ki67. FIG. 9A shows that both harmine and the TGFβ inhibitor GW788388 induced beta cell proliferation, whereas the combination of harmine and GW788388 was additive. Next, human cadaveric islets were transplanted into NOD-SCID mice. FIG. 9B shows that although the control rate of beta cell proliferation was higher than is typical for adult human beta cells (i.e., greater than 0.1-0.2%), harmine increased this rate, GW788388 had no effect, and the harmine-GW788388 combination had a synergistic effect on human islets in vivo.

Discussion of Examples 1-6

Figure 8A:
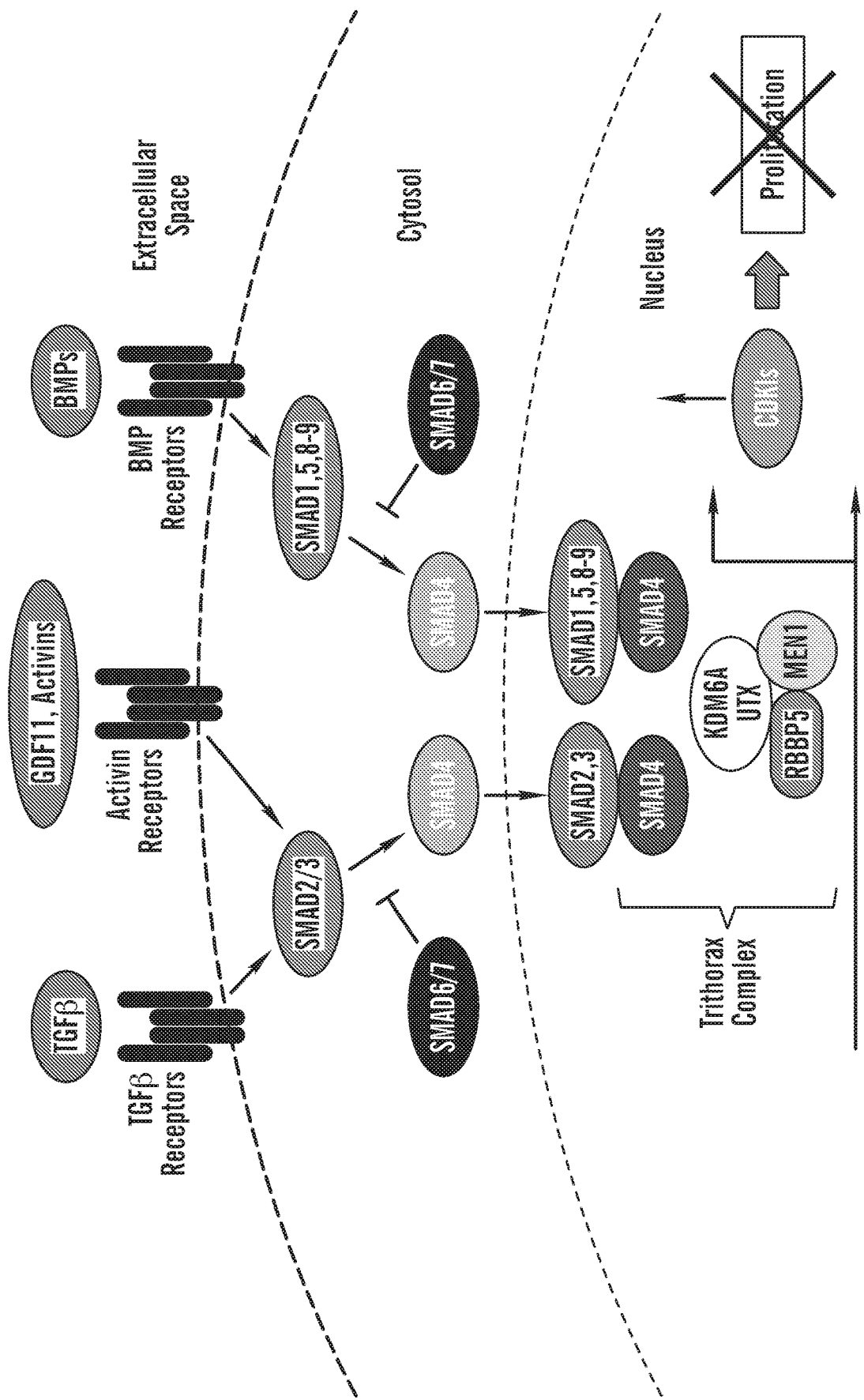
FIGS. 8A-8B are models of TGFβ superfamily signaling and Harmine-TGFβ superfamily actions on human beta cell proliferation.
Figure 8B:
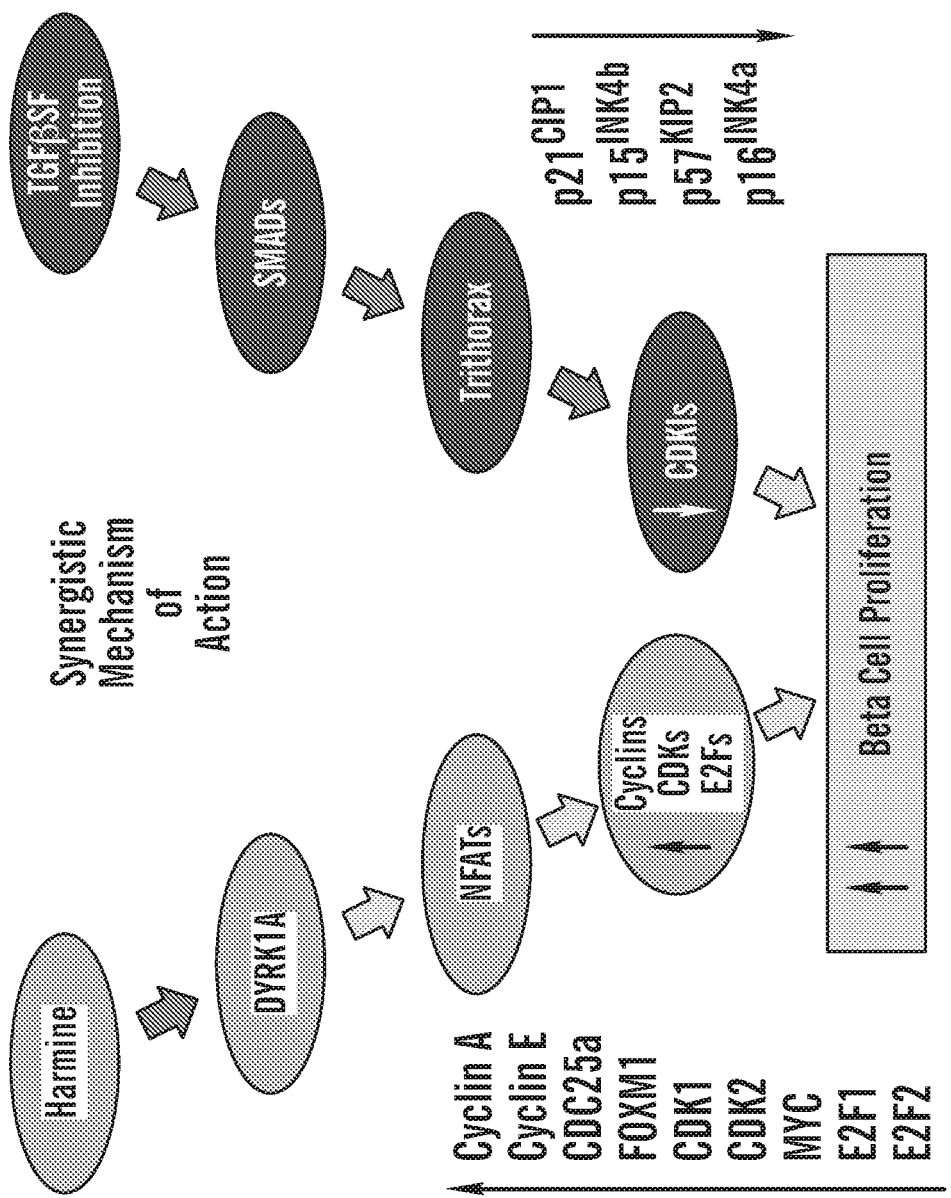

Examples 1-6 provide various novel, unanticipated, and important observations. First, they describe a novel combination of two classes of molecules—a DYRK1A inhibitor coupled with a TGFβ superfamily inhibitor—that that reliably induce "rates" of proliferation in mature adult human beta cells averaging 5-8% per day, rates that have not previously been observed with any class of therapeutic molecules. These rates exceed normal physiological pancreatic beta cell replication in the first year of life (Gregg et al., "Formation of a Human Beta Cell Population Within Pancreatic Islets is Set Early in Life," *J. Clin. Endocrinol. Metab.* 97:3197-3206 (2012); Meier et al., "Beta Cell Replication is the Primary Mechanism Subserving the Postnatal Expansion of Beta Cell Mass in Humans," *Diabetes* 57:1584-94 (2008); and Kassem et al., "Beta-Cell Proliferation and Apoptosis in the Developing Normal Human Pancreas and in Hyperinsulinism of Infancy," *Diabetes* 49:1325-1333 (2000), which are hereby incorporated by reference in their entirety). Second, the above examples demonstrate that the DYRK1A inhibitor-TGFβSF inhibitor combination behaves in a synergistic manner to drive human beta cell proliferation and provide novel mechanisms and models for this synergy (FIG. 8A). Third, the above examples document that the beneficial effects on human proliferation are achieved, in part, via modulation of the activities of chromatin-modifying, epigenetic modulating enzymes of the Trithorax family, and extend Trithorax beta cell modulatory involvement to KDM6A and likely additional members (FIG. 8B). Fourth, the above examples demonstrate that beta cell proliferation generated by the harmine-TGFβSF inhibitor combination is not associated with beta cell de-differentiation, but rather favors maintained or increased beta cell differentiation. Fifth, the beneficial effects of the DYRK1A inhibitor-TGFβSF inhibitor combination extend to beta cells from people with T2D. Sixth, the above examples add leucettine-41 (Tahtouh et al., "Selectivity, Co-Crystal Structures and Neuroprotective Properties of Leucettines, a Family of Protein Kinase Inhibitors Derived from the Marine Sponge Alkaloid Leucettamine B," *J. Med. Chem.* 55:9312-30 (2012), which is hereby incorporated by reference in its entirety) to the growing list of small molecule DYRK1A inhibitors that are able to activate human beta cell proliferation. Seventh, the induction of proliferation using two different in vivo models is confirmed. Eighth, the observations suggest that locally produced endogenous TGFβSF agonists such as TGFβ's activins, inhibins, BMPs and related molecules play an important role in restraining proliferation in the adult human beta cell, and that this inhibitory pathway can be manipulated for therapeutic purposes. Finally, while DYRK1A remains a central target of harmine and other DYRK1A inhibitors, the above examples suggest that DYRK1A inhibitors may also act in part via SMAD pathways as well.

While DYRK1A inhibitors such as harmine, 5-IT, INDY, GNF4877 have been shown to induce replication in human beta cells (Wang et al., "A High-Throughput Chemical Screen Reveals That Harmine-Mediated Inhibition of DYRK1A Increases Human Pancreatic Beta Cell Replication," *Nature Medicine* 21:383-388 (2015); Shen et al., "Inhibition of DYRK1A and GSK3B Induces Human Beta Cell Proliferation," *Nature Comm.* 6:8372, DOI: 10-1038/ncomm9372 October (2015); Dirice et al., "Inhibition of DYRK1A Stimulates Human Beta Cell Proliferation," *Diabetes* 65:1660-71 (2016); Aamodt et al., "Development of a Reliable Automated Screening System to Identify Small Molecules and Biologics That Promote Human Beta Cell Regeneration," *AJP Endo. Metab.* 311:E859-68 (2016); and Wang et al., "Single Cell Mass Cytometry Analysis of Human Endocrine Pancreas," *Cell Metabolism* 24:616-26 (2016), which are hereby incorporated by reference in their entirety), in general "rates" of proliferation or labeling indices have been low, in the 1.5-3%/day range. Thus, while DYRK1A inhibition-induced beta cell proliferation is an important advance, one might envision higher rates of proliferation as being required for therapeutic human beta cell expansion in T1D and T2D. The average "rates" in the 5-8% range obtained with the DYRK1A inhibitor-TGFβ inhibitor combination (FIGS. 1A-B and FIGS. 2A-G) are notable in this regard.

TGFβ inhibitors and SMAD inhibition are well known as activators of proliferation in rodent islets (Mukherjee et al., "FSTL3 Deletion Reveals Roles for TGFbeta Family Ligands in Glucose and Fat Homeostasis in Adults." *Proc. Natl. Acad. Sci.* 104:1348-53 (2007); Brown & Schneyer, "Emerging Roles for the TGFb Superfamily in Pancreatic Beta Cell Homeostasis," *Trends Endocrinol. Metab.* 21:441-448 (2010); El-Gohary et al., "A Smad Signaling Network Regulates Islet Proliferation," *Diabetes* 63:224-36 (2014); Xiao et al., "Transient Suppression of Transforming Growth Factor Beta Receptor Signaling Facilitates Human Islet Transplantation," *Endocrinology* 157:1348-56 (2016); Xiao et al., "M2 Macrophages Promote Beta Cell Proliferation by Upregulation of SMAD7," *Proc. Natl. Acad. Sci.* 111: E1211-20 (2014); Smart et al., "Conditional Expression of Smad7 in Pancreatic Beta Cells Disrupts TGF-beta Signaling and Induces Reversible Diabetes Mellitus," *PLoS Biology* 4:e39 (2006); Zhou et al., "Combined Modulation of Polycomb and Trithorax Genes Rejuvenates Beta Cell Replication," *J. Clin. Invest.* 123:4849-58 (2013); Dhawan et al., "Inhibition of TGF-Beta Signaling Promotes Human Pancreatic Beta Cell Replication," *Diabetes* 65:1208-18 (2016); and Brown et al., "Effects of Activin A on Survival, Function and Gene Expression of Pancreatic Islets from Normal and Diabetic Human Donors," *Islets* 6:5-6 (2014), which are hereby incorporated by reference in their entirety). For example, knockout of the endogenous activin inhibitor, follistatin-like-3, leads to beta cell expansion in mouse genetic models (Mukherjee et al., "FSTL3 Deletion Reveals Roles for TGFbeta Family Ligands in Glucose and Fat Homeostasis in Adults." *Proc. Natl. Acad. Sci.* 104:1348-53 (2007), which are hereby incorporated by reference in their entirety). Others have reported that spontaneous or inducible upregulation of the I-SMAD, SMAD7, is associated with beta cell proliferation and expansion in mice (El-Gohary et al., "A Smad Signaling Network Regulates Islet Proliferation," *Diabetes* 63:224-36 (2014) and Smart et al., "Conditional Expression of Smad7 in Pancreatic Beta Cells Disrupts TGF-beta Signaling and Induces Reversible Diabetes Mellitus," *PLoS Biology* 4:e39 (2006), which are hereby incorporated by reference in their entirety). Still others have used small molecule TGFβ receptor inhibitors to activate proliferation in mouse pancreatic beta cells (El-Gohary et al., "A Smad Signaling Network Regulates Islet Proliferation," *Diabetes* 63:224-36 (2014) and Smart et al., "Conditional Expression of Smad7 in Pancreatic Beta Cells Disrupts TGF-beta Signaling and Induces Reversible Diabetes Mellitus," *PLoS Biology* 4:e39 (2006), which are hereby incorporated by reference in their entirety). When examined in adult human islets, however, beta cell proliferation in response to TGFβSF inhibitors has been modest or negligible (Dhawan et al., "Inhibition of TGF-Beta Signaling Promotes Human Pancreatic Beta Cell Replication," *Diabetes* 65:1208-18 (2016), which is hereby incorporated by reference in its entirety), a result confirmed here (FIG. 1A).

The principal advance of the present invention was to employ TGFβ inhibitors in combination with harmine, a concept derived from human insulinoma data mining where both DYRK1A and SMAD pathway abnormalities are evident (Wang et al., "Insights Into Beta Cell Regeneration for Diabetes Via Integration of Molecular Landscapes in Human Insulinomas," *Nature Communications*, 8:767 (2017), which is hereby incorporated by reference in its entirety). Moreover, the above examples demonstrate that inhibiting any of the various classes of TGFβ superfamily receptors, including TGFβ, activin, and BMP receptors, in the presence of harmine, are all effective in permitting beta cell proliferation. As reported previously (Brown & Schneyer, "Emerging Roles for the TGFβ Superfamily in Pancreatic Beta Cell Homeostasis," *Trends Endocrinol. Metab.* 21:441-448 (2010), which is hereby incorporated by reference in its entirety), that TGFβ superfamily members and SMAD signaling pathways are abundant in human islets. It is inferred that these collectively comprise an inhibitory regulatory pathway that restrains human beta cell proliferation, perhaps, as suggested by others, to protect against de-differentiation (El-Gohary et al., "A Smad Signaling Network Regulates Islet Proliferation," *Diabetes* 63:224-36 (2014) and Smart et al., "Conditional Expression of Smad7 in Pancreatic Beta Cells Disrupts TGF-beta Signaling and Induces Reversible Diabetes Mellitus," *PLoS Biology* 4:e39 (2006), which are hereby incorporated by reference in their entirety).

It is now found that a DYRK1A inhibitor/TGFβSF inhibitor combination is not merely additive, but clearly synergistic (FIGS. 1A-B and FIGS. 2A-G). DYRK1A inhibitors seem to preferentially activate cell cycle activators, such as cyclins and cdks, whereas the TGFβSF inhibitors seem to preferentially repress cell cycle inhibitors, notably CDKN1A, CDKN1C, and CDKN2B, effects that appear to be mediated, at least for CDKN1A and CDKN1C, by SMAD signaling and Trithorax chromatin remodeling (FIG. 8B). Involvement of CDKN2B and CDKN2A is possible but more difficult to demonstrate because they arise from a common locus that encodes additional cell cycle modulators such as $p14^{ARF}$, ANRIL, and others. These issues, and the unusually GC-rich nature of this locus, make selective silencing of individual members of this locus challenging.

The involvement of the Trithorax family of epigenetic modifying genes in controlling beta cell growth is not unexpected: the canonical Trithorax member, MEN1, was positionally cloned from people with the Multiple Endocrine Neoplasia type 1 syndrome (Chandrasekharappa et al., "Positional Cloning of the Gene for Multiple Endocrine Neoplasia-Type 1," *Science* 276:404-407 (1997), which is hereby incorporated by reference in its entirety), which includes insulinomas, and MEN1, and other Trithorax members have been shown to regulate beta cell proliferation and mass in animal models and cell lines (Crabtree et al., "A Mouse Model of Multiple Endocrine Neoplasia Type 1 Develops Multiple Endocrine Tumors," *PNAS* 98:1118-23 (2001); Crabtree et al., "Of Mice and MEN1: Insulinomas in a Conditional Mouse Knockout," *Mol. Cell Biol.* 23:6075-6085 (2003); Chen et al., "PDGF Controls Age-Dependent Proliferation in Pancreatic Beta Cells," *Nature* 478:349-55 (2011); Chen et al., "Polycomb Protein ezh2 Regulates Pancreatic Beta Cell Ink4a/Arf Expression and Regeneration in Diabetes Mellitus," *Genes and Development* 23:975-985 (2009); and Karnick et al., "Menin Regulates Pancreatic Islet Growth by Promoting Histone Methylation and Expression of Genes Encoding p27kip1 and p18Ink4c," *PNAS USA* 102:14659-64 (2005), which are hereby incorporated by reference in their entirety). Moreover, MEN1 and other Trithorax members, such as MLL's have also been shown to participate in rodent beta cell proliferation and ChIP to cell cycle inhibitors (Zhou et al., "Combined Modulation of Polycomb and Trithorax Genes Rejuvenates Beta Cell Replication," *J. Clin. Invest.* 123:4849-58 (2013) and Dhawan et al., "Inhibition of TGF-Beta Signaling Promotes Human Pancreatic Beta Cell Replication," *Diabetes* 65:1208-18 (2016), which are hereby incorporated by reference in their entirety). In addition, another Trithorax member, KDM6A, has recently been shown to be inactivated in occasional human insulinomas, and silencing or pharmacologically inhibiting KDM6A in human beta cells and block expression of the cell cycle inhibitor CDKN1C (Wang et al., "Insights Into Beta Cell Regeneration for Diabetes Via Integration of Molecular Landscapes in Human Insulinomas," *Nature Communications*, 8:767 (2017), which is hereby incorporated by reference in its entirety). The present invention extends these observations by showing that the DYRK1A inhibitor/TGFβSF inhibitor combination disrupts normal binding of MEN1 and KDM6A to CDKN1A and CDKN1C promoters and enhancers, providing for the first time a direct demonstration of Trithorax modulation of the key cell cycle inhibitor CDKN1C in human beta cells. It is predicted that TGFβSF and SMAD targets are not limited to Trithorax members, and likely include other epigenetic modifying genes, such as members of the Polycomb Repressive Complexes (PRCs). Indeed, canonical PRC members such as EZH2 and BMI1 are well known age-related modifiers of rodent beta cell proliferation (Chen et al., "PDGF Controls Age-Dependent Proliferation in Pancreatic Beta Cells," *Nature* 478:349-55 (2011); Chen et al., "Polycomb Protein ezh2 Regulates Pancreatic Beta Cell Ink4a/Arf Expression and Regeneration in Diabetes Mellitus," *Genes and Development* 23:975-985 (2009); and Karnick et al., "Menin Regulates Pancreatic Islet Growth by Promoting Histone Methylation and Expression of Genes Encoding p27kip1 and p18Ink4c," *PNAS USA* 102:14659-64 (2005), which are hereby incorporated by reference in their entirety), and bind to and oppose Trithorax actions on many genes (Zhou et al., "Combined Modulation of Polycomb and Trithorax Genes Rejuvenates Beta Cell Replication," *J. Clin. Invest.* 123: 4849-58 (2013) and Dhawan et al., "Inhibition of TGF-Beta Signaling Promotes Human Pancreatic Beta Cell Replication," *Diabetes* 65:1208-18 (2016), which are hereby incorporated by reference in their entirety). Further, there is recurrent evidence of PRC mutation and mis-expression in human insulinomas (Wang et al., "Insights Into Beta Cell Regeneration for Diabetes Via Integration of Molecular Landscapes in Human Insulinomas," *Nature Communications*, 8:767 (2017), which is hereby incorporated by reference in its entirety), and EZH2 overexpression in combination with CDKN1C silencing has been reported to enhance human beta cell proliferation (Wang et al., "Insights Into Beta Cell Regeneration for Diabetes Via Integration of Molecular Landscapes in Human Insulinomas," *Nature Communications*, 8:767 (2017), which is hereby incorporated by reference in its entirety).

Type II diabetes is associated in mouse and humans beta cells with de-differentiation to a more primitive, and poorly functional, insulin-depleted neuroendocrine cell type (Talchai et al., "Pancreatic Beta Cell Dedifferentiation as a Mechanism of Diabetic Beta Cell Failure," *Cell* 150:1223-34 (2012) and Cinti et al., "Evidence of Beta Cell Dedifferentiation in Human Type 2 Diabetes," *J. Clin. Endocrinol. Metab.* 101:1044-54 (2016), which are hereby incorporated by reference in their entirety). As was the case with harmine, the harmine-TGFβSF inhibitor combination increases several key markers of human beta cell identity, differentiation and maturity, including NKX6.1, PDX1, MAFA, MAFB, SLC2A2, and PCSK2. It is presumed, but not experimentally confirmed, that this relates in part to DYRK1A inhibition with resultant NFaT nuclear translocation and binding to promote this class of genes, as documented in mouse beta cells (Heit et al., "Calcineurin/NFAT Signaling Regulates Pancreatic β-Cell Growth and Function," *Nature* 443:345-349 (2006) and Goodyer et al., "Neonatal Beta Cell Development in Mice and Humans is Regulated by Calcineurin/NFaT," *Developmental Cell* 23:21-34 (2012), which are hereby incorporated by reference in their entirety). From a therapeutic standpoint, this induction of differentiation is important and remains surprising, because conventional wisdom suggests that events that drive beta cell proliferation will inevitably lead to beta cell de-differentiation and functional failure. The fact that differentiated molecular phenotype and glucose-stimulated insulin secretion remain intact despite induction of proliferation (FIGS. 4A-F) is encouraging. This ability of the harmine-TGFβSF inhibitor combination to drive both beta cell proliferation as well as enhance differentiation markers in T2D islets is both surprising and welcome: It bodes well for treatment of people with T2D.

While it seems clear that harmine and related compounds work principally to drive proliferation principally via inhibition of DYRK1A (Wang et al., "A High-Throughput Chemical Screen Reveals That Harmine-Mediated Inhibition of DYRK1A Increases Human Pancreatic Beta Cell Replication," *Nature Medicine* 21:383-388 (2015); Shen et al., "Inhibition of DYRK1A and GSK3B Induces Human Beta Cell Proliferation," *Nature Comm.* 6:8372, DOI: 10-1038/ncomm9372 October (2015); and Dirice et al., "Inhibition of DYRK1A Stimulates Human Beta Cell Proliferation," *Diabetes* 65:1660-71 (2016), which are hereby incorporated by reference in their entirety), it was surprising to observe that harmine reduced phospho-SMAD3, as well as SMADs1,5,8/9. This suggests that in addition to its effects on DYRK1A, harmine and other DYRK1A inhibitors likely interact with SMAD signaling in ways that remain to be elucidated.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of increasing cell proliferation in a population of human pancreatic beta cells, said method comprising:
contacting a population of human pancreatic beta cells with a dual-specificity tyrosine phosphorylation-regulated kinase 1A (DYRK1A) inhibitor selected from the group consisting of harmine, INDY, and leucettine and a transforming growth factor beta (TGFβ) superfamily signaling pathway inhibitor selected from the group consisting of LY364947 and GW788388 under conditions effective to increase cell proliferation in the population of pancreatic beta cells, wherein said contacting increases the number of proliferating pancreatic beta cells in the population by at least about 5% per day.

2. The method according to claim 1, wherein said method is carried out in vivo.

3. The method according to claim 1, wherein said contacting is carried out with a composition comprising both the DYRK1A inhibitor and the TGFβ superfamily signaling pathway inhibitor.

4. The method according to claim 1, wherein said contacting increases the number of proliferating pancreatic beta cells in the population by at least about 6% per day.

5. The method according to claim 1, wherein the TGFβ superfamily signaling pathway inhibitor is GW78838.

6. The method according to claim 1, wherein said contacting is carried out with harmine and LY364947.

7. The method according to claim 1, wherein said contacting is carried out with harmine and GW788388.

8. The method according to claim 1, wherein said pancreatic beta cells are primary human pancreatic beta cells.

9. The method according to claim 1, wherein said contacting does not induce beta cell death or DNA damage.

10. The method according to claim 1, wherein said contacting induces beta cell differentiation.

11. The method according to claim 1, wherein said contacting increases glucose-stimulated insulin secretion.

12. A method of treating a human subject for a condition associated with insufficient insulin secretion, said method comprising:
administering to a human subject in need of treatment for a condition associated with an insufficient level of insulin secretion a dual-specificity tyrosine phosphorylation-regulated kinase 1A (DYRK1A) inhibitor selected from the group consisting of harmine, INDY, and leucettine and a TGFβ superfamily signaling pathway inhibitor selected from the group consisting of LY364947 and GW788388 under conditions effective to increase pancreatic beta cell mass in the subject to treat the human subject for an insufficient level of insulin secretion, wherein said administering increases the number of proliferating pancreatic beta cells in the subject by at least about 5% per day.

13. The method according to claim 12, wherein the subject is treated for Type I diabetes.

14. The method according to claim 12, wherein the subject is treated for Type II diabetes.

15. The method according to claim 12, wherein said administering is carried out orally, transdermally, parenterally, subcutaneously, intravenously, intramuscularly, or intraperitoneally.

16. The method according to claim 12, wherein said administering increases the number of proliferating pancreatic beta cells in the subject by at least about 6% per day.

17. The method according to claim 12, wherein said administering increases glucose-stimulated insulin secretion in pancreatic beta cells of the subject.

18. The method according to claim 12, wherein the TGFβ superfamily signaling pathway inhibitor is GW788388.

19. The method according to claim 12, wherein said administering is carried out by administering a composition comprising both the DYRK1A inhibitor and the TGFβ superfamily signaling pathway inhibitor.

20. The method according to claim 12, wherein said administering is carried out with harmine and LY364947.

21. The method according to claim 12, wherein said administering is carried out with harmine and GW788388.

22. A composition comprising:
a dual-specificity tyrosine phosphorylation-regulated kinase 1A (DYRK1A) inhibitor selected from the group consisting of harmine, INDY, and leucettine and
a transforming growth factor beta (TGFβ) superfamily signaling pathway inhibitor selected from the group consisting of LY364947 and GW788388.

23. The composition according to claim 22 further comprising:
a carrier.

24. The composition according to claim 22, wherein the carrier is a pharmaceutically-acceptable carrier.

* * * * *

SEQUENCE LISTING

```
<160> NUMBER OF SEQ ID NOS: 17

<210> SEQ ID NO 1
<211> LENGTH: 21
<212> TYPE: DNA
<213> ORGANISM: Homo sapien

<400> SEQUENCE: 1
gctgtaatct gaagatcttc a                                              21
```

```
<210> SEQ ID NO 2
<211> LENGTH: 21
<212> TYPE: DNA
<213> ORGANISM: Homo sapien

<400> SEQUENCE: 2
gcaacctgaa gatcttcaac a                                              21

<210> SEQ ID NO 3
<211> LENGTH: 21
<212> TYPE: DNA
<213> ORGANISM: Homo sapien

<400> SEQUENCE: 3
ggaattgatc tctcaggatt a                                              21

<210> SEQ ID NO 4
<211> LENGTH: 21
<212> TYPE: DNA
<213> ORGANISM: Homo sapien

<400> SEQUENCE: 4
cgctctacat cttctgcctt a                                              21

<210> SEQ ID NO 5
<211> LENGTH: 21
<212> TYPE: DNA
<213> ORGANISM: Homo sapien

<400> SEQUENCE: 5
attctgcacg agaaggtaca c                                              21

<210> SEQ ID NO 6
<211> LENGTH: 20
<212> TYPE: DNA
<213> ORGANISM: Homo sapien

<400> SEQUENCE: 6
atgatctcag ctcactgcaa                                                20

<210> SEQ ID NO 7
<211> LENGTH: 20
<212> TYPE: DNA
<213> ORGANISM: Homo sapien

<400> SEQUENCE: 7
acagggtcag gagttttgag                                                20

<210> SEQ ID NO 8
<211> LENGTH: 21
<212> TYPE: DNA
<213> ORGANISM: Homo sapien

<400> SEQUENCE: 8
ggctgcctct gctcaataat g                                              21

<210> SEQ ID NO 9
<211> LENGTH: 19
<212> TYPE: DNA
<213> ORGANISM: Homo sapien

<400> SEQUENCE: 9
ccagcacttc ctctcccctt                                                19
```

<210> SEQ ID NO 10
<211> LENGTH: 19
<212> TYPE: DNA
<213> ORGANISM: Homo sapien

<400> SEQUENCE: 10
ctccccaaag taaacagac						19

<210> SEQ ID NO 11
<211> LENGTH: 20
<212> TYPE: DNA
<213> ORGANISM: Homo sapien

<400> SEQUENCE: 11
ccagcccttt ggatggtttg						20

<210> SEQ ID NO 12
<211> LENGTH: 24
<212> TYPE: DNA
<213> ORGANISM: Homo sapien

<400> SEQUENCE: 12
ctgctggaac tcggccaggc tcag					24

<210> SEQ ID NO 13
<211> LENGTH: 24
<212> TYPE: DNA
<213> ORGANISM: Homo sapien

<400> SEQUENCE: 13
tgagctgcgc cagctgaggt gtga					24

<210> SEQ ID NO 14
<211> LENGTH: 18
<212> TYPE: DNA
<213> ORGANISM: Homo sapien

<400> SEQUENCE: 14
ctaaaacaag ggtttgcg						18

<210> SEQ ID NO 15
<211> LENGTH: 24
<212> TYPE: DNA
<213> ORGANISM: Homo sapien

<400> SEQUENCE: 15
ctagatccta gtcctgtctt gaac					24

<210> SEQ ID NO 16
<211> LENGTH: 20
<212> TYPE: DNA
<213> ORGANISM: Homo sapien

<400> SEQUENCE: 16
acttgtccct aggaaaatcc						20

```
<210> SEQ ID NO 17
<211> LENGTH: 20
<212> TYPE: DNA
<213> ORGANISM: Homo sapien

<400> SEQUENCE: 17
gaaaacggag agtgagtttg                                              20
```